United States Patent
Rapraeger

(10) Patent No.: US 9,550,816 B2
(45) Date of Patent: Jan. 24, 2017

(54) SYNDECAN PEPTIDES AND POLYPEPTIDES AS INHIBITORS OF CANCER

(71) Applicant: Wisconsin Alumni Research Foundation, Madison, WI (US)

(72) Inventor: Alan Rapraeger, Stoughton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/688,703

(22) Filed: Apr. 16, 2015

(65) Prior Publication Data

US 2015/0218237 A1 Aug. 6, 2015

Related U.S. Application Data

(62) Division of application No. 13/936,872, filed on Jul. 8, 2013, now Pat. No. 9,034,828.

(60) Provisional application No. 61/784,930, filed on Mar. 14, 2013, provisional application No. 61/669,551, filed on Jul. 9, 2012.

(51) Int. Cl.
| | |
|---|---|
| *C07K 14/00* | (2006.01) |
| *C07K 14/47* | (2006.01) |
| *C07K 14/705* | (2006.01) |
| *A61K 38/17* | (2006.01) |
| *A61K 38/00* | (2006.01) |

(52) U.S. Cl.
CPC ........... *C07K 14/47* (2013.01); *A61K 38/1709* (2013.01); *C07K 14/4703* (2013.01); *C07K 14/70596* (2013.01); *A61K 38/00* (2013.01); *C07K 2319/23* (2013.01)

(58) Field of Classification Search
None
See application file for complete search history.

(56) References Cited

PUBLICATIONS

Amin et al., "Tumor endothelial cells express epidermal growth factor receptor (EGFR) but not ErbB3 and are responsive to EGF and to EGFR kinase inhibitors," *Cancer Res.*, 66(4):2173-2180, 2006.
Beauvais and Rapraeger, "Syndecan-1 couples the insulin-like growth factor-1 receptor to inside-out integrin activation," *J Cell Sci*, 123(21):3796-807, 2010.
Beauvais et al., "Syndecan-1 regulates $\alpha_v\beta_3$ and $\alpha_v\beta_5$ integrin activation during angiogenesis and is blocked by synstatin, a novel peptide inhibitor," *J. Exp. Med.*, 206(3):691-705, 2009.
Böhling et al., "Expression of growth factors and growth factor receptors in capillary hemangioblastoma," *J Neuropathol Exp Neurol*, 1996. 55(5):522-7, 1996.
Bruns et al., "Blockade of the epidermal growth factor receptor signaling by a novel tyrosine kinase inhibitor leads to apoptosis of endothelial cells and therapy of human pancreatic carcinoma," *Cancer Res.*, 60(11):2926-2935, 2000.
Dermer, "Another anniversary of the war on cancer," *Bio/Technology*, 12:320, 1994.
Freshney, In: *Culture of Animal Cells, A Manual of Basic Technique*, Alan R. Liss, Inc., New York, pp. 3-4, 1983.
Gura, "Systems for identifying new drugs are often faulty," *Science*, 278:1041-1042, 1997.
Huang et al., "Molecular inhibition of angiogenesis and metastatic potential in human squamous cell carcinomas after epidermal growth factor receptor blockade," *Mol. Cancer Ther.*, 1(7):507-514, 2002.
Jain, "Barriers to drug delivery in solid tumors," *Scientific American*, 271(1):58-65, 1994.
Kedar et al., "Blockade of the epidermal growth factor receptor signaling inhibits angiogenesis leading to regression of human renal cell carcinoma growing orthotopically in nude mice," *Clin. Cancer Res.*, 8(11):3592-3600, 2002.
Nikolopoulos et al., "Integrin beta4 signaling promotes tumor angiogenesis," *Cancer Cell*, 6(5):471-483, 2004.
Russell et al., "Alpha 6 beta 4 integrin regulates keratinocyte chemotaxis through differential GTPase activation and antagonism of alpha 3 beta 1 integrin," *J. Cell Sci.*, 116(Pt 17):3543-3556, 2003.
Sehgal et al., "Integrin beta4 regulates migratory behavior of keratinocytes by determining laminin-332 organization," *J. Biol. Chem.*, 281(46):35487-35498, 2006.
Wang et al., "Interaction of syndecan and alpha6beta4 integrin cytoplasmic domains: regulation of ErbB2-mediated integrin activation," *J. Biol. Chem.*, 285:13569-13579, 2010.
Whiteford and Couchman, "A conserved NXIP motif is required for cell adhesion properties of the syndecan-4 ectodomain," *J Biol Chem*, 281(43):32156-63, 2006.

*Primary Examiner* — Sheela J Huff
(74) *Attorney, Agent, or Firm* — Boyle Fredrickson, S.C.

(57) ABSTRACT

The invention provides for peptides from syndecan 4 and methods of use therefor. These peptides can inhibit α6β4 integrin interaction with EGFR, thereby preventing tumor cell growth and tissue invasion.

21 Claims, 15 Drawing Sheets

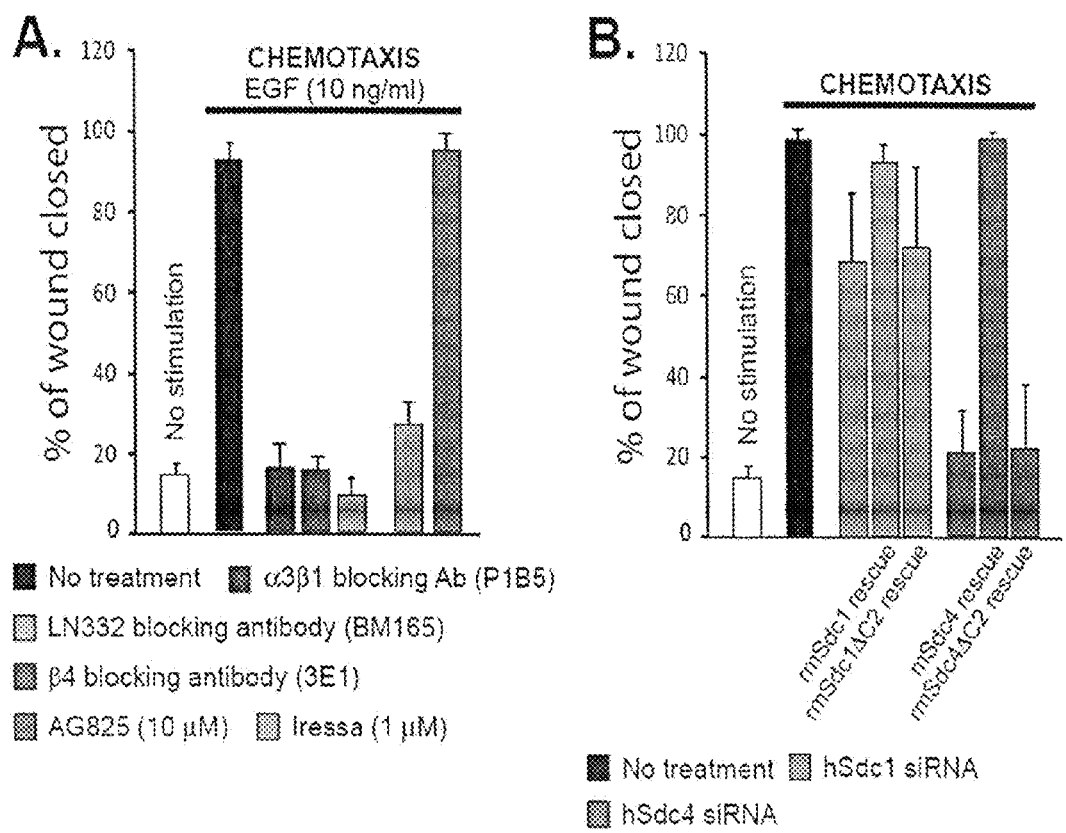
FIG. 4A-B

A.

```
            C1                    V                      C2
Sdc1  RMKKKDEGSYSLEEPKQANGGAYQKPTKQEEFYA³⁰¹

Sdc4  RMKKKDEGSYDLG-KKP---IYKKAPTN--EFYA¹⁹⁸
```

B.

$A^{1729}$  $A^{1733}$

β4 ....TRHVTQEFVSRTLTTSGTLSTHMDQQFFQT$^{1752}$

↑
truncate
Δ1729-1752

FIG. 5A-B

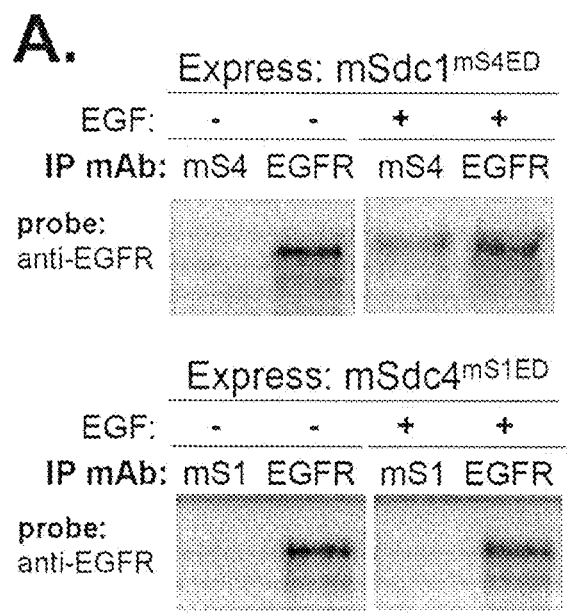
FIG. 6A-B

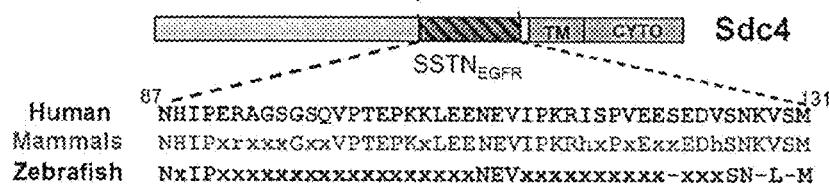
FIG. 8A-C

SEQUENCE LISTING

<160> NUMBER OF SEQ ID NOS: 16

<210> SEQ ID NO 1
<211> LENGTH: 198
<212> TYPE: PRT
<213> ORGANISM: Homo sapiens

<400> SEQUENCE: 1

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
    130                 135                 140

Glu Val Leu Ala Ala Leu Ile Val Gly Gly Ile Val Gly Ile Leu Phe
145                 150                 155                 160

Ala Val Phe Leu Ile Leu Leu Leu Met Tyr Arg Met Lys Lys Lys Asp
                165                 170                 175

Glu Gly Ser Tyr Asp Leu Gly Lys Lys Pro Ile Tyr Lys Lys Ala Pro
            180                 185                 190

Thr Asn Glu Phe Tyr Ala
        195

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
ggaggaattc tatgcctga                                                19

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

<400> SEQUENCE: 3
caggaatctg atgactttga g                                             21

<210> SEQ ID NO 4
<211> LENGTH: 45
<212> TYPE: PRT
<213> ORGANISM: Homo sapiens

```
<400> SEQUENCE: 4

Asn His Ile Pro Glu Arg Ala Gly Ser Gly Ser Gln Val Pro Thr Glu
1               5                   10                  15

Pro Lys Lys Leu Glu Glu Asn Glu Val Ile Pro Lys Arg Ile Ser Pro
                20                  25                  30

Val Glu Glu Ser Glu Asp Val Ser Asn Lys Val Ser Met
                35                  40                  45

<210> SEQ ID NO 5
<211> LENGTH: 67
<212> TYPE: PRT
<213> ORGANISM: Homo sapiens

<400> SEQUENCE: 5

Val Val His Pro Leu Val Pro Leu Asp Asn His Ile Pro Glu Arg Ala
1               5                   10                  15

Gly Ser Gly Ser Gln Val Pro Thr Glu Pro Lys Lys Leu Glu Glu Asn
                20                  25                  30

Glu Val Ile Pro Lys Arg Ile Ser Pro Val Glu Glu Ser Glu Asp Val
                35                  40                  45

Ser Asn Lys Val Ser Met Ser Ser Thr Val Gln Gly Ser Asn Ile Phe
    50                  55                  60

Glu Arg Thr
65

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Ser Asn Lys Val Ser Met
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 7

Val Pro Thr Glu Pro Lys Xaa Leu Glu Glu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Ala Ala Ala Ala Ala Ala Ala Ala Ala Ala
1               5                   10

<210> SEQ ID NO 9
```

```
<211> LENGTH: 34
<212> TYPE: PRT
<213> ORGANISM: Artificial Sequence
<220> FEATURE:
<223> OTHER INFORMATION: Synthetic peptide

<400> SEQUENCE: 9

Arg Met Lys Lys Lys Asp Glu Gly Ser Tyr Ser Leu Glu Glu Pro Lys
1               5                   10                  15

Gln Ala Asn Gly Gly Ala Tyr Gln Lys Pro Thr Lys Gln Glu Glu Phe
            20                  25                  30

Tyr Ala

<210> SEQ ID NO 10
<211> LENGTH: 28
<212> TYPE: PRT
<213> ORGANISM: Artificial Sequence
<220> FEATURE:
<223> OTHER INFORMATION: Synthetic peptide

<400> SEQUENCE: 10

Arg Met Lys Lys Lys Asp Glu Gly Ser Tyr Asp Leu Gly Lys Lys Pro
1               5                   10                  15

Ile Tyr Lys Lys Ala Pro Thr Asn Glu Phe Tyr Ala
            20                  25

<210> SEQ ID NO 11
<211> LENGTH: 30
<212> TYPE: PRT
<213> ORGANISM: Artificial Sequence
<220> FEATURE:
<223> OTHER INFORMATION: Synthetic peptide

<400> SEQUENCE: 11

Thr Arg His Val Thr Gln Glu Phe Val Ser Arg Thr Leu Thr Thr Ser
1               5                   10                  15

Gly Thr Leu Ser Thr His Met Asp Gln Gln Phe Phe Gln Thr
            20                  25                  30

<210> SEQ ID NO 12
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
```

```
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid

<400> SEQUENCE: 12

Asn His Ile Pro Xaa Leu Xaa Xaa Xaa Gly Xaa Xaa Val Pro Thr Glu
1               5                   10                  15

Pro Lys Xaa Leu Glu Glu Asn Glu Val Ile Pro Lys Arg Xaa Xaa Pro
            20                  25                  30

Xaa Glu Xaa Xaa Glu Asp Xaa Ser Asn Lys Val Ser Met
            35                  40                  45

<210> SEQ ID NO 13
<211> LENGTH: 42
<212> TYPE: PRT
<213> ORGANISM: Danio rerio
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(22)
<223> OTHER INFORMATION: Xaa can be any naturally occurring amino acid
<220> FEATURE:
<221> NAME/KEY: misc_feature
<222> LOCATION: (26)..(38)
<223> OTHER INFORMATION: Xaa can be any naturally occurring amino acid

<400> SEQUENCE: 13

Asn Xaa Ile Pro Xaa Xaa Xaa Xaa Xaa Xaa Xaa Xaa Xaa Xaa Xaa Xaa
1               5                   10                  15

Xaa Xaa Xaa Xaa Xaa Xaa Asn Glu Val Xaa Xaa Xaa Xaa Xaa Xaa Xaa
            20                  25                  30

Xaa Xaa Xaa Xaa Xaa Xaa Ser Asn Leu Met
            35                  40

<210> SEQ ID NO 14
<211> LENGTH: 45
<212> TYPE: PRT
<213> ORGANISM: Artificial Sequence
<220> FEATURE:
<223> OTHER INFORMATION: Synthetic peptide

<400> SEQUENCE: 14

Asn His Ala Pro Glu Arg Ala Gly Ser Gly Ser Gln Val Pro Thr Glu
1               5                   10                  15

Pro Lys Lys Leu Glu Glu Asn Glu Val Ile Pro Lys Arg Ile Ser Pro
            20                  25                  30

Val Glu Glu Ser Glu Asp Val Ser Asn Lys Val Ser Met
            35                  40                  45

<210> SEQ ID NO 15
<211> LENGTH: 45
<212> TYPE: PRT
<213> ORGANISM: Artificial Sequence
<220> FEATURE:
<223> OTHER INFORMATION: Synthetic peptide

<400> SEQUENCE: 15

Asn His Ile Pro Glu Arg Ala Gly Ser Gly Ser Gln Ala Ala Ala Ala
```

-continued

```
1               5                   10                  15
Ala Ala Ala Ala Ala Ala Asn Glu Val Ile Pro Lys Arg Ile Ser Pro
            20                  25                  30
Val Glu Glu Ser Glu Asp Val Ser Asn Lys Val Ser Met
        35                  40                  45

<210> SEQ ID NO 16
<211> LENGTH: 39
<212> TYPE: PRT
<213> ORGANISM: Artificial Sequence
<220> FEATURE:
<223> OTHER INFORMATION: Synthetic peptide

<400> SEQUENCE: 16

Asn His Ile Pro Glu Arg Ala Gly Ser Gly Ser Gln Val Pro Thr Glu
1               5                   10                  15
Pro Lys Lys Leu Glu Glu Asn Glu Val Ile Pro Lys Arg Ile Ser Pro
            20                  25                  30
Val Glu Glu Ser Glu Asp Val
        35
```

SYNDECAN PEPTIDES AND POLYPEPTIDES AS INHIBITORS OF CANCER

PRIORITY CLAIM

The present application is a divisional of U.S. application Ser. No. 13/936,872, filed Jul. 8, 2013, which claims benefit of priority to U.S. Provisional Application No. 61/669,551, filed Jul. 9, 2012, and U.S. Provisional Application No. 61/784,930, filed Mar. 14, 2013, the entire contents of each application being hereby incorporated by reference.

FEDERAL FUNDING CLAUSE

This invention was made with government support under CA109010 and CA139872 awarded by the National Institutes of Health. The government has certain rights in the invention.

SEQUENCE LISTING

Pursuant to 37 C.F.R. 1.821(c), a sequence listing is submitted herewith as an ASCII compliant text file named "WARFP0046USD1.txt" created on Apr. 8, 2015 and having a size of ~9 KB. The content of the aforementioned file is hereby incorporated by reference in its entirety.

BACKGROUND OF THE INVENTION

1. Field of the Invention

This invention relates to regulation of cell growth, and more particularly to regulation of cancer cell growth. In particular, peptides and polypeptides derived from particular regions of the syndecan 4 molecule has been shown to inhibit engagement of $\alpha 6\beta 4$ integrin by EGFR, thereby limiting tissue invasion and tumor cell growth and/or survival.

2. Related Art

It is well established that the EGFR family of receptor tyrosine kinases, in particular EGFR and HER2, have major roles in human cancer (Hynes and Lane, 2005; Hynes and MacDonald, 2009; Scaltriti and Baselga, 2006), notably breast cancer, head and neck squamous cell carcinoma (HNSCC), and lung cancer for EGFR. EGFR is a causal agent in triple negative (ER-, PR-, HER2-) breast cancer (also classified as "basaloid"), which comprises 15-25% of breast cancers (Herschkowitz et al., 2007; Livasy et al., 2006; Perou et al., 2000; Teng et al., 2011). The triple negative (TN) tumors are especially malignant, often strike younger women (especially African-Americans) and are resistant to tamoxifen therapy (Livasy et al., 2006; Diaz et al., 2005; Haupt et al., 2010; Lu et al., 2008; Carvalho et al., 2010; Friedrichs et al., 1995), the common mode of treatment for most women. These women usually present as node-positive at first diagnosis and often die of metastatic disease (Dent et al., 2007; Haffty et al., 2006). EGFR has also long been recognized to play a central role in progression of squamous cell carcinoma of the head and neck (H&N), in which it is overexpressed in over 80% of the tumors, and the negative response of H&N patients to therapy (Chang and Califano, 2008; Perez-Ordonez et al., 2006). It is commonly hyperactivated by overexpression of its ligands (e.g., EGF, TGFα), by activating EGFR mutations, and by its overexpression (Chung et al., 2004; Grandis et al., 1997, Cassell and Grandis, 2010. Furthermore, γ-irradiation, the treatment of choice for many tumors, leads to EGFR activation by a variety of mechanisms (Zimmerman et al., 2006)—including increased EGFR expression (Schmidt-Ullrich et al., 1994), inhibition of phosphatases that would otherwise maintain receptor quiescence, and promoting the shedding (e.g., activation) of the membrane-anchored pro-forms of EGFR ligands (Dent et al., 1999)—leading to significantly poorer 5-yr survival rates in patients with EGFR-positive tumors.

The $\alpha 6\beta 4$ integrin and its ligand LN332 are upregulated in breast and squamous cell carcinomas, and are linked to invasion, metastasis and recurrent disease (Choi and Chen, 2005; Ginos et al., 2004; Patarroyo et al., 2002; Wilhelmsen et al., 2006). Identified as the TSP-180 antigen in mouse tumors (Falcioni et al., 1986), or the A9 antigen in humans (Van Waes et al., 1991; Kimmel and Carey, 1986), high expression of this antigen predicts a higher rate of early relapse in H&N cancer patients (Wolf et al., 1990; Carey et al., 1987). In more recent studies exploring its tumor-promoting role using animal models, keratinocytes that lack expression of the β4 integrin subunit fail to form invasive squamous cell carcinomas when transformed with ras and IκB, unlike their normal counterparts that express the integrin (Dajee et al., 2003; Tran et al., 2008). Despite this seeming importance of the integrin in squamous cell carcinoma, there currently are no therapeutics available to target its tumor-promoting activities.

A number of labs have investigated the potential role of syndecans in $\alpha 6\beta 4$-mediated cell migration and tumorigenesis. But these studies have focused largely on syndecans acting as co-receptors with the $\alpha 6\beta 4$ integrin in laminin binding rather than a role in directly regulating $\alpha 6\beta 4$ activation. The phosphorylated and "activated" $\alpha 6\beta 4$ integrin redistributes to the leading edges of invading keratinocytes or tumors; these leading edges overexpress the "unprocessed" form of LN332 that retains the LG4,5 heparin-binding region that engages syndecans (Amano et al., 2000; Marinkovich et al., 1992; Matsui et al., 1995; Goldfinger et al., 1999; Goldfinger et al., 1998). Interestingly, recent work from Rouselle's group shows that Sdc1 and Sdc4 bind differently to the LG4,5 domain and speculates that this may account for somewhat different cell behaviors mediated by these two syndecans (Carulli et al., 2012). Other work shows that expression of LG4,5 supports tumorigenesis in an animal model of squamous cell carcinoma, again suggesting a potential role for syndecans in tumorigenesis (Tran et al., 2008), although it is admittedly indirect.

Although not widely appreciated, the $\alpha 6\beta 4$ integrin is also expressed on vascular endothelial cells in vivo, where its function in hemidesmosomes allows the endothelium to resist frictional forces as it does on stratified epithelia. Giancotti has shown a clear role for $\alpha 6\beta 4$ integrin in tumor angiogenesis and that $\alpha 6\beta 4$ is expressed in the vasculature of several tumor types (prostate, breast, glioma, papillary thyroid, melanoma) (Nikolopoulos et al., 2004). Although not studied extensively, it clear that endothelial cells express EGFR family members (Amin et al., 2006) and that tumor endothelial cells upregulate the expression of EGFR in particular (Amin et al., 2006; Bohling et al., 1996; Bruns et al., 2000; Kedar et al., 2002; Huang et al., 2002). Despite this seeming importance of the integrin in squamous cell carcinoma and tumor-induced angiogenesis, there currently are no therapeutics available to target its tumor-promoting activities.

Work from a variety of laboratories has shown a linkage between the $\alpha 6\beta 4$ integrin and EGFR in breast and other cancers (Lu et al., 2008; Folgiero et al., 2008). This integrin in normal cells assembles with laminin in the basement membrane underlying basal epithelial cells as well as endothelial cells lining blood vessels, forming stable hemidesmosomes in which the long (ca. 1000 amino acid) cytoplasmic domain of the β4 subunit anchors to the keratin filament network in the cytoplasm of the cell (Wilhelmsen et al., 2006; Hopkinson and Jones, 2000; Nievers et al., 1999). In contrast to this "stabilizing" role, however, the integrin takes part in the invasion, proliferation and survival of tumors that overexpress the receptor tyrosine kinases HER2, EGFR, or c-Met—leading to the assembly of these kinases with the integrin (Wilhelmsen et al., 2006; Agazie and Hayman, 2003; Mainiero et al., 1996; Mariotti et al., 2001; Bertotti et al., 2005; Bertotti et al., 2006; Bon et al., 2007; Falcioni et al., 1997; Gambaletta et al., 2000; Santoro et al., 2003; Trusolino et al., 2001; Tsuruta et al., 2008; Giancotti, 2007). There is evidence for this in TN breast tumors, especially, as α6β4 integrin and EGFR overexpression are causally linked in this disease and lead to poor prognosis (Lu et al., 2008). When coupled with the integrin, signaling from these kinases disrupts the hemidesmosome (Rabinovitz et al., 2004; Wilhelmsen et al., 2007) and leads to tyrosine phosphorylation of the β4 cytoplasmic domain, providing docking sites for signaling effectors that drive tumor cell proliferation, invasion and survival (Wilhelmsen et al., 2006; Mariotti et al., 2001; Bertotti et al., 2006; Wilhelmsen et al., 2007; Mainiero et al., 1997; Shaw et al., 1997; Guo et al., 2006; Merdek et al., 2007; Dutta and Shaw, 2008; Datta et al., 1999; Dans et al., 2001; Shaw, 2001; Yang et al., 2010). The distal third of the β4 tail containing these phosphorylation sites has thus been termed the β4 "signaling domain" (Guo et al., 2006) (FIG. 1). In studies using the MMTV-Neu mouse model of HER2+ breast cancer, replacement of native β4 with a β4 mutant ($\beta^{1355T}$) lacking this signaling domain acts as a suppressor of breast cancer (Guo et al., 2006), suggesting that the wild type β4 receptor normally couples with HER2 to drive tumorigenesis of HER2+ breast cancer as well. Work utilizing a number of mammary carcinoma cell lines, focusing mostly on HER2+ cells, also shows that HER2/α6β4 signaling is critical for invasion and survival of these tumors (Falcioni et al., 1997; Gambaletta et al., 2000; Guo et al., 2006). Complementing their expression in the tumors, HER2 and EGFR are also expressed in endothelial cells, especially those induced by tumors (Amin et al., 2006; Bruns et al., 2000; Kedar et al., 2002), and couple with the α6β4 integrin during tumor-induced angiogenesis (Nikolopoulos et al., 2004).

SUMMARY OF THE INVENTION

Thus, in accordance with the present invention there is provided an isolated and purified peptide segment consisting of between 25 and 100 amino acid residues and comprising about 45 residues of SEQ ID NO:1 including residues 87-131 (SEQ ID NO: 4). The peptide may be 45, 46, 47, 48, 49, 50, 51, 52, 53, 54, 55, 60, 65, 70, 75, 80, 85, 90, 95 or 100 amino acid residues in length. The peptide may be between 45 and 54 amino acid residues in length, between 31 and 40 amino acid residues, 45 and 65 amino acid residues in length or between 45 and 75 amino acid residues in length. The peptide may consists essentially of or consist of residues 87-131 (SEQ ID NO: 4). The peptide may consist of essentially of or consist of residues 78-131 (SEQ ID NO: 5). The peptide may comprise all D amino acid, all L amino acids, or a mixture of D and L amino acids.

Also provided is a nucleic acid encoding a peptide segment consisting of between 45 and 100 amino acid residues and comprising about 45 residues of SEQ ID NO:1 including residues 87-131 (SEQ ID NO: 4). The encoded peptide may be 45, 46, 47, 48, 49, 50, 51, 52, 53, 54, 55, 60, 65, 70, 75, 80, 85, 90, 95 or 100 amino acid residues in length. The encoded peptide may be between 31 and 40 amino acid residues, 45 and 54 amino acid residues in length, between 45 and 65 amino acid residues in length or between 45 and 75 amino acid residues in length. The encoded peptide may consists essentially of or consist of residues 87-131 (SEQ ID NO: 4). The encoded peptide may consist of essentially of or consist of residues 78-131 (SEQ ID NO: 5). The nucleic acid may be in operable connection to a promoter, and/or located in a replicable vector, such as a viral vector.

In another embodiment, there is provided a method of inhibiting α6β4 integrin interaction with EGFR comprising contacting a EGFR molecule with a peptide segment consisting of between 45 and 100 amino acid residues and comprising about 45 residues of SEQ ID NO:1 including residues 87-131 (SEQ ID NO: 4). The peptide may be 45, 46, 47, 48, 49, 50, 51, 52, 53, 54, 55, 60, 65, 70, 75, 80, 85, 90, 95 or 100 amino acid residues in length. The peptide may be between 31 and 40 amino acid residues, between 45 and 54 amino acid residues in length, between 45 and 65 amino acid residues in length or between 45 and 75 amino acid residues in length. The peptide may consists essentially of or consist of residues 87-131 (SEQ ID NO: 4). The peptide may consist of essentially of or consist of residues 78-131 (SEQ ID NO: 5). The peptide may comprise all D amino acid, all L amino acids, or a mixture of D and L amino acids. The α6β4 integrin may be located on the surface of a cell, such as a cancer cell, such as a carcinoma, a myeloma, a melanoma, a schwannoma, a malignant peripheral nerve sheath tumor cell or a glioma. The cancer cell may bea metastatic cancer cell or a tumor stem cell. The method may further comprise contacting said cancer cell with a second cancer inhibitory agent. Contacting may comprise providing to said cell an expression construct comprising a nucleic acid encoding said peptide segment operably linked to a promoter active in said cell.

Another embodiment encompasses a method of screening for an agent that inhibits the binding of syndecan-4 and EGFR comprising (a) providing a syndecan-4 or a fragment thereof and a EGFR or a fragment thereof, wherein said syndecan-4 or a fragment thereof and a EGFR or a fragment thereof are capable of binding each other; (b) contacting the proteins or fragments of step (a) with a candidate substance; and (c) assessing the binding of said syndecan-4 or a fragment thereof and said EGFR or a fragment thereof, wherein reduced binding in step (c) as compared to the binding in the absence of said candidate substance identifies said candidate substance as an agent that inhibits the binding of syndecan-4 and EGFR. The candidate substance may be a protein, a peptide, a peptidometic, a polynucleotide, an oligonucleotide, or a small molecule. One or both of said syndecan-4 or a fragment thereof and/or said EGFR or a fragment thereof may be labeled with a detectable label. Step (c) may comprise FRET, immunodetection, a gel-shift assay, or a phosphorylation assay. The candidate substance is a peptide segment consisting essentially of or consisting of residues 87-131 (SEQ ID NO: 4) or 78-131 (SEQ ID NO: 5). Step (a) may further comprise including α6β4 or a fragment thereof that interacts with syndecan-1 and/or EGFR. The method may further comprise a control reaction of assessing the binding of said syndecan-4 or a fragment thereof and said EGFR or a fragment thereof in the absence of said candidate substance. Steps (a)-(c) may be performed in a cell-free system or may be performed in a cell or may be performed in vivo.

In yet a further embodiment, there is provide a method of treating a subject with a cancer, cancer cells of which express α6β4 integrin and EGFR, comprising contacting said cells with a peptide segment consisting of between 45 and 100 amino acid residues and comprising about 45 residues of SEQ ID NO:1 including residues 87-131 (SEQ ID NO: 4). The peptide may be 45, 46, 47, 48, 49, 50, 51, 52, 53, 54, 55, 60, 65, 70, 75, 80, 85, 90, 95 or 100 amino acid residues in length. The peptide may be between 31 and 40 amino acid residues in length, between 45 and 54 amino acid residues in length, between 45 and 65 amino acid residues in length or between 45 and 75 amino acid residues in length. The peptide may consists essentially of or consist of residues 87-131 (SEQ ID NO: 4). The peptide may consist of essentially of or consist of residues 78-131 (SEQ ID NO: 5). The peptide may comprise all D amino acid, all L amino acids, or a mixture of D and L amino acids. The subject may be a non-human mammal, such as a human. The cancer may be a carcinoma, a myeloma, a melanoma or a glioma. The peptide may be administered directly to said cancer cells, local to said cancer cells, regional to said cancer cells, or systemically. The method may further comprise administering to said subject a second cancer therapy selected from chemotherapy, radiotherapy, immunotherapy, hormonal therapy, or gene therapy. The method may further comprise administering said peptide to said subject more than once.

In still another embodiment, there is provided a method of inhibiting scarring in a subject to comprising administering to said subject a peptide segment consisting of between 45 and 100 amino acid residues and comprising about 45 residues of SEQ ID NO:1 including residues 87-131 (SEQ ID NO: 4). The peptide may be 45, 46, 47, 48, 49, 50, 51, 52, 53, 54, 55, 60, 65, 70, 75, 80, 85, 90, 95 or 100 amino acid residues in length. The peptide may be between 45 and 54 amino acid residues in length, between 45 and 65 amino acid residues in length or between 45 and 75 amino acid residues in length. The peptide may consists essentially of or consist of residues 87-131 (SEQ ID NO: 4). The peptide may consist of essentially of or consist of residues 78-131 (SEQ ID NO: 5). The peptide may comprise all D amino acid, all L amino acids, or a mixture of D and L amino acids.

An additional embodiment comprises a method of inhibiting pathologic neovascularization comprising administering to said subject a peptide segment consisting of between 45 and 100 amino acid residues and comprising about 45 residues of SEQ ID NO:1 including residues 87-131 (SEQ ID NO: 4). The peptide may be 45, 46, 47, 48, 49, 50, 51, 52, 53, 54, 55, 60, 65, 70, 75, 80, 85, 90, 95 or 100 amino acid residues in length. The peptide may be between 45 and 54 amino acid residues in length, between 45 and 65 amino acid residues in length or between 45 and 75 amino acid residues in length. The peptide may consists essentially of or consist of residues 87-131 (SEQ ID NO: 4). The peptide may consist of essentially of or consist of residues 78-131 (SEQ ID NO: 5). The peptide may comprise all D amino acid, all L amino acids, or a mixture of D and L amino acids. The pathologic may neovascularization involves activated vascular endothelial cells.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of the invention that follows.

FIGS. 4A-B. Sdc4 is required for EGFR/α6β4-dependent HaCat keratinocyte migration. (FIG. 4A) HaCat keratinocytes deposit laminin 332 (LN332) and migrate upon this using α3β1 and α6β4 integrins to close a scratch wound in the monolayer. Migration induced by addition of 10 ng/ml EGF (EGF-mediated chemotaxis) is blocked by antibodies against either integrin, or by BM165 which targets their binding site in LN332. Note that EGF chemotaxis depends on EGFR, as it is blocked by 1 µM Iressa (also called "gefitinib), which blocks EGFR and not by the tyrphostin AG825 that blocks HER2 kinase expressed by these cells but plays a role in haptotactic migration by these cells. (FIG. 4B) The potential roles of Sdc1 (as a control) or Sdc4 in wound closure is tested by silencing their expression, together with attempting to rescue with either wild-type mouse Sdc1 or Sdc4, or mouse mutants unable to engage the β4 cytoplasmic domain (mSdc1ΔC2 or mSdc4ΔC2). EGF-induced chemotaxis is blocked by silencing endogenous Sdc4, and this cannot be rescued by Sdc4ΔC2 that fails to engage the α6β4 integrin. Silencing Sdc1 has only a minor effect, indicating that the EGFR/α6β4 complex is regulated by its interaction with Sdc4.

FIGS. 5A-B. Sdc4-specific binding site in β4 integrin cytoplasmic domain. (FIG. 5A) Syndecans. The entire cytoplasmic domains of Sdc1 (SEQ ID NO: 9) and Sdc4 (SEQ ID NO: 10) are shown (Rapraeger & Ott, 1998). C1 and C2 regions are conserved across the syndecan family, whereas the V region is syndecan-specific. (FIG. 5B) β4 integrin. The last 30 amino acids of the β4 cytoplasmic domain (over 1,000 amino acids long) are shown (SEQ ID NO: 11), focusing on the last 24 amino acids necessary to bind Sdc1 and Sdc4, as the $β4^{\Delta 1729\text{-}1752}$ truncation mutant fails to bind either syndecan. Mutation of E1729 to alanine (E1729A) specifically disrupts binding to Sdc4 and the R1733A mutant fails to bind Sdc1.

FIGS. 6A-B. S1ED and S4ED capture HER2 and EGFR, respectively, from cell lysates. (FIG. 6A) Mouse syndecan chimeras in which their ectodomains are switched are expressed in HaCat cells, then immunoprecipitated with antibodies specific for the mouse syndecan ectodomains. Note that EGFR co-precipitate with mSdc1 bearing the mSdc4 ectodomain (precipitated by mS4 antibody), and mSdc4 no longer captures these receptors when its ectodomain is swapped for that of Sdc1. Also note that these complexes assemble only upon EGF treatment. (FIG. 6B) Recombinant Sdc1 and Sdc4 ectodomains (GST-S1ED and GST-S4ED) on glutathione beads are incubated with lysates of EGF-stimulated A431 carcinoma cells, then analyzed for the capture of HER2 or EGFR on western blots. HER2 or EGFR are immun0precipitated from the lysates directly for comparison. Note that S1ED captures only HER2 and S4ED captures only EGFR.

FIGS. 8A-C. Schematic summary of experiments using either recombinant GST fusion proteins or synthetic peptides to disrupt Sdc4-dependent coupling of EGFR to α6β4 integrin necessary for EGF-stimulated cell migration. GST-fusion proteins or synthetic peptides were added at concentrations ranging from 0.1 to 30 µM to the culture medium of human HaCat keratinocytes or MCF10A mammary epithelial cells in the presence or absence of 20 ng/ml EGF. The ability of the constructs to inhibit the migration of the cells to close a scratch wound in confluent monolayers was determined and express as the concentration of inhibitor necessary to cause 50% inhibition of cell migration. (FIG. 8A) Competition using recombinant GST-fusion proteins. GST-Sdc4 fusion proteins bearing truncations or mutations were assessed for their competitive activity. Proteins that retained the sequence from amino acids 87 to 131 (SEQ ID NO: 4) were found to fully active, tentatively identifying this as the active site. (FIG. 8B) Schematic representation of the active site in Sdc4. The active site is shown as a juxtamembrane site in the ectodomain of Sdc4. TM is the transmembrane domain and CYTO is the cytoplasmic domain. The sequence of a peptide derived from this site ($SSTN_{EGFR}$) (SEQ ID NO: 4) is shown along with its homology across other mammalian Sdc4 species (SEQ ID NO: 12) and its homology to Sdc4 derived from zebrafish (SEQ ID NO: 13), identifying highly conserved amino acids at the extreme N- and C-terminus of the peptide. (FIG. 8C) Competition with synthetic peptides. Peptides were purchased from commercial sources for testing as a putative synstatin inhibitory peptide ($SSTN_{EGFR}$). Mutation of isoleucine at position 89 to alanine (I89A), or mutation of amino acids 99-108 to alanine (99-108A) reduce the activity by 10-fold. Truncation of amino acids 126-131 at the C-terminus (Δ126-131) reduces the activity by at least 100-fold.

(FIG. 9A) HaCat human keratinocytes, an example of a normal stratified epithelium, (FIG. 9B) UM-SCC47 cells, a squamous cell carcinoma derived from the tongue of a male patient (a stratified epithelium), (FIG. 9C) SCC25 cells, another squamous cell carcinoma from the tongue of a male patient), (FIG. 9D) MCF10A cells, a normal human breast epithelium, (FIG. 9E) MDA-MB-468 cells, a triple-negative (TN) breast carcinoma, and (FIG. 9F) SKBr3 cells, a HER2+ human breast carcinoma. Note that all four carcinomas are inhibited by $SSTN_{EGFR}$, and this is enhanced when $SSTN_{EGFR}$ is combined with the other SSTN peptides, leading to obvious cell death (e.g., the number of cells at the end of the experiment are less than at the beginning).

DESCRIPTION OF ILLUSTRATIVE EMBODIMENTS

It is increasingly appreciated that growth factor receptors and extracellular matrix receptors work closely together to regulate cell proliferation, invasion and survival, and may do so as macromolecular assemblies at the cell surface. Indeed, as discussed extensively above, EGFR is known to be coupled with the α6β4 integrin and signaling from this receptor assembly is implicated in both tumorigenesis and tumor-induced angiogenesis. However, the means by which these receptors are coupled remains largely unknown.

The inventor has now discovered that the EGFR/α6β4 integrin assembly is regulated by yet another class of receptors—the syndecan family of matrix receptors. In this novel mechanism, syndecan-4 (Sdc4) links the α6β4 integrin to EGFR—linkage that is required for tumor cell survival. Importantly, the linkage relies on a highly specific motif in the extracellular domain of Sdc4. This motif, when supplied as a soluble peptide, competes with the signaling from the Sdc4-coupled α6β4 integrin/EGFR complex, presumably by disrupting their association with the syndecan. This inhibitory activity is designated "synstatin-EGFR" (abbreviated $SSTN_{EGFR}$).

Figure 1:
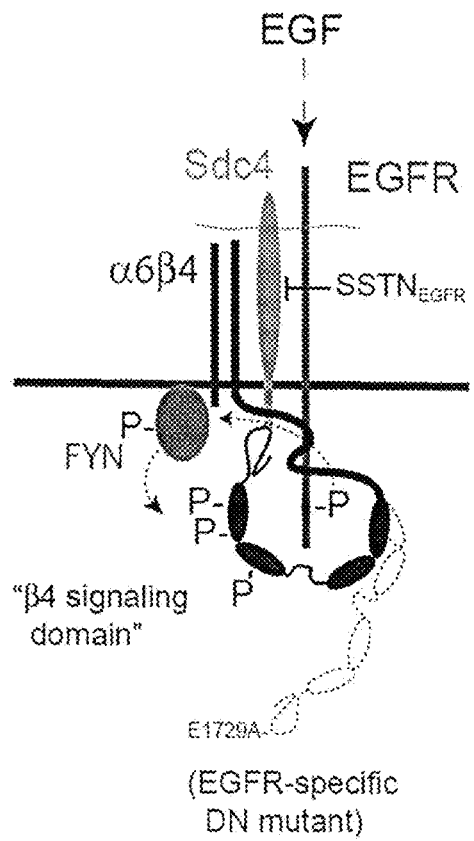
FIG. 1. Putative model of syndecan-coupling of α6β4 integrin and EGFR in carcinoma and angiogenic endothelial cells. The inventor's findings show that Sdc4 couples EGFR to the α6β4 integrin. This integrin, together with the α3β1 integrin, is a receptor for LN332 in epithelial cells and endothelial cells. When activated by this kinase, the α6β4 integrin participates in matrix adhesion and signaling necessary for cell migration, but is also critical for cell survival in tumors. EGFR "activates" the α6β4 integrin via its activation of Fyn (Mariotti et al., 2001; Guo et al., 2006; Wang et al., 2010), which phosphorylates several tyrosines in the "β4 signaling domain" (see arrows). Sdc4 binding the β4 integrin cytoplasmic domain is critical for this signaling cascade, ostensibly by bringing the "signaling domain" to the membrane where it can be phosphorylated by Fyn (Mariotti et al., 2001). Mutation of E1729 (E1729A) in the β4 integrin cytoplasmic domain disrupts Sdc4 binding. This mutant acts as a dominant negative mutant to specifically disrupt the function of the Sdc4-coupled mechanism during cell migration and tumor cell survival. An extracellular interaction with Sdc4 is also critical for the assembly and function of this complex—potentially acting to capture EGFR with the integrin. Recombinant fragments of the Sdc4 ectodomain block the function of the Sdc4-coupled EGFR complex. This blocking activity is a putative new synstatin ($SSTN_{EGFR}$) that is proposed to inhibit tumor growth, survival and invasion, and tumor-induced angiogenesis.

This interaction is illustrated in the model of Sdc4 provided in FIG. 1. All four members of the syndecan family engage the cytoplasmic domain of the β4 integrin, but the focus here will be on Sdc4, which is expressed on epithelial cells (Bernfield et al., 1992; David et al., 1992) and co-immunoprecipitates with the α6β4 integrin and EGFR from activated keratinocytes, A431 cervical carcinoma cells, breast carcinoma cells and HN squamous carcinoma cells (our preliminary data) (FIGS. 4A-B and Table I). Importantly, EGFR docks only with Sdc4/α6β4 and not with the other syndecans. The interaction site capturing the EGFR appears to be in the Sdc4 extracellular domain, which is distinct from that of other syndecans, and the inventor finds that recombinant Sdc4 peptides mimicking these interaction sites (e.g., $SSTN_{EGFR}$) block this interaction. In addition to this extracellular site, the inventor finds that the syndecans also engage distinct sites in the β4 cytoplasmic domain. Sdc4 binding its site in the β4 tail is essential for signaling by this complex, as mutation of this Sdc4-specific site generates a β4 dominant-negative mutant that specifically blocks the Sdc4-coupled signaling mechanism.

I. SYNDECANS

A. The Syndecan Family

Cell surface adhesion receptors physically bind cells to their extracellular matrix (ECM) and couple such interactions to intracellular signaling mechanisms which influence gene expression, cell morphology, motility, growth, differentiation and survival (Roskelley et al., 1995; Miranti and Brugge, 2002). Many ECM ligands contain closely spaced proteoglycan- and integrin-binding domains, indicating that the molecular mechanisms by which cells recognize and interact with their extracellular milieu may involve the formation of signaling complexes containing both proteoglycans and integrins. Consequentially, these two types of receptors may act in concert to modulate cell adhesion and migration. While the role of integrins in cell adhesion and signaling is well established, the role of heparan sulfate proteoglycans (HSPGs) is not well characterized.

The vertebrate syndecans are a family of four transmembrane HSPGs. Endowed by their heparan sulfate (HS) chains, syndecans bind a variety of ECM ligands, including fibronectin (FN), laminin (LN), tenascin, thrombospondin (TSP), vitronectin (VN) and the fibrillar collagens (COL) (Bernfield et al., 1999). While the syndecan HS chains are essential for matrix binding, less is known about the role of syndecan core proteins in cell adhesion signaling, although the core protein can affect ligand binding interactions, as well as occupancy induced signaling (Rapraeger and Ott, 1998; Rapraeger, 2000).

The syndecans display a high degree of conservation within their core proteins both across species and across family members. Like the integrins, the syndecans lack intrinsic signaling activity. Their short cytoplasmic tails (ca. 30 aa) consist of three regions, two of which are conserved amongst the four syndecans (C1 and C2) and which flank an intervening variable (V) region. Proteins known to interact with these conserved domains are believed to link syndecan ligand binding interactions to the transduction of intracellular signals (Couchman et al., 2001). Each family member is uniquely defined by its ectodomains and the V-regions of its cytoplasmic tail. Divergence within these regions is believed to confer separate and distinct functions to each individual family member. Distinct roles for the V-regions of Sdc-2 and -4 in matrix assembly and focal adhesion formation respectively have been described (Klass et al., 2000; Woods and Couchman, 2001); however, specific functions for the syndecan ectodomains are almost wholly unknown with the noted exception of Sdc-1 and -4 which contain binding sites for as yet unidentified cell surface receptor(s) (McFall and Rapraeger, 1997; McFall and Rapraeger, 1998).

B. Syndecan Function in Cell Adhesion and Spreading

Current evidence suggests that the syndecan core proteins participate in adhesion-mediated signaling in collaboration with co-receptors at the cell surface. One example is Sdc-4 in focal adhesion and stress fiber formation, which requires both Sdc-4 and integrin engagement whereas neither is sufficient alone (Woods et al., 1986; Izzard et al., 1986; Streeter and Rees, 1987; Singer et al., 1987). The requirement for Sdc-4 ligation can be overcome by treatment with phorbol esters (Woods and Couchman, 1994) or lysophosphatidic acid (LPA) (Saoncella et al., 1999) implicating PKC and RhoA in Sdc-4 signaling. While the mechanism by which Sdc-4 contributes to RhoA activation is not clear, it is known that Sdc-4 interacts directly with PKCα as well as phosphatidyl inositol 4,5 bisphosphate (PIP2) via its cytoplasmic tail and these interactions potentiate PKCα activity (Oh et al., 1997a; Oh et al., 1997b; Oh et al., 1998; Baciu and Goetinck, 1995).

C. Syndecan-4

Syndecan-4 is a protein that in humans is encoded by the SDC4 gene. This gene is found on chromosome 20, while a pseudogene has been found on chromosome 22. Syndecan-4 is a transmembrane (type I) heparan sulfate proteoglycan that functions as a receptor in intracellular signaling. The protein is found as a homodimer and is a member of the syndecan proteoglycan family. Syndecan-4 is upregulated in osteoarthritis and inhibition of syndecan-4 reduces cartilage destruction in mouse models of OA.

II. INTEGRINS AND EGFR

A. α6β4 Integrin

Integrins are receptors that mediate attachment between a cell and the tissues surrounding it, which may be other cells or the ECM. They also play a role in cell signaling and thereby regulate cellular shape, motility, and the cell cycle.

Typically, receptors inform a cell of the molecules in its environment and the cell responds. Not only do integrins perform this outside-in signalling, but they also operate an inside-out mode. Thus, they transduce information from the ECM to the cell as well as reveal the status of the cell to the outside, allowing rapid and flexible responses to changes in the environment, for example to allow blood coagulation by platelets.

There are many types of integrins, and many cells have multiple types on their surface. Integrins are of vital importance to all animals and have been found in all animals investigated, from sponges to mammals. Integrins have been extensively studied in humans.

Integrins work alongside other proteins such as cadherins, immunoglobulin superfamily cell adhesion molecules, selectins and syndecans to mediate cell-cell and cell-matrix interaction and communication. Integrins bind cell surface and ECM components such as fibronectin, vitronectin, collagen, and laminin.

B. EGFR

The epidermal growth factor receptor (EGFR; ErbB-1; HER1 in humans) is the cell-surface receptor for members of the epidermal growth factor family (EGF-family) of extracellular protein ligands. The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). Mutations affecting EGFR expression or activity could result in cancer.

EGFR (epidermal growth factor receptor) exists on the cell surface and is activated by binding of its specific ligands, including epidermal growth factor and transforming growth factor α (TGFα). ErbB2 has no known direct activating ligand, and may be in an activated state constitutively or become active upon heterodimerization with other family members such as EGFR. Upon activation by its growth factor ligands, EGFR undergoes a transition from an inactive monomeric form to an active homodimer—although there is some evidence that preformed inactive dimers may also exist before ligand binding. In addition to forming homodimers after ligand binding, EGFR may pair with another member of the ErbB receptor family, such as ErbB2/Her2/neu, to create an activated heterodimer. There is also evidence to suggest that clusters of activated EGFRs form, although it remains unclear whether this clustering is important for activation itself or occurs subsequent to activation of individual dimers.

EGFR dimerization stimulates its intrinsic intracellular protein-tyrosine kinase activity. As a result, autophosphorylation of several tyrosine (Y) residues in the C-terminal domain of EGFR occurs. These include Y992, Y1045, Y1068, Y1148 and Y1173. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation. Such proteins modulate phenotypes such as cell migration, adhesion, and proliferation. Activation of the receptor is important for the innate immune response in human skin. The kinase domain of EGFR can also cross-phosphorylate tyrosine residues of other receptors it is aggregated with, and can itself be activated in that manner.

Mutations that lead to EGFR overexpression (known as upregulation) or overactivity have been associated with a number of cancers, including lung cancer, anal cancers and glioblastoma multiforme. In this latter case a more or less specific mutation of EGFR, called EGFRvIII is often observed. Mutations, amplifications or misregulations of EGFR or family members are implicated in about 30% of all epithelial cancers.

Mutations involving EGFR could lead to its constant activation, which could result in uncontrolled cell division—a predisposition for cancer. Consequently, mutations of EGFR have been identified in several types of cancer, and it is the target of an expanding class of anticancer therapies.

The identification of EGFR as an oncogene has led to the development of anticancer therapeutics directed against EGFR, including gefitinib and erlotinib for lung cancer, and cetuximab for colon cancer.

Many therapeutic approaches are aimed at the EGFR. Cetuximab and panitumumab are examples of monoclonal antibody inhibitors. However the former is of the IgG1 type, the latter of the IgG2 type; consequences on antibody-dependent cellular cytotoxicity can be quite different. Other monoclonals in clinical development are zalutumumab, nimotuzumab, and matuzumab. The monoclonal antibodies block the extracellular ligand binding domain. With the binding site blocked, signal molecules can no longer attach there and activate the tyrosine kinase.

Another method is using small molecules to inhibit the EGFR tyrosine kinase, which is on the cytoplasmic side of the receptor. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (mixed EGFR and ERBB2 inhibitor) are examples of small molecule kinase inhibitors.

There are several quantitative methods available that use protein phosphorylation detection to identify EGFR family inhibitors. New drugs such as IRESSA and Tarceva directly target the EGFR. Patients have been divided into EGFR-positive and EGFR-negative, based upon whether a tissue test shows a mutation. EGFR-positive patients have shown an impressive 60% response rate, which exceeds the response rate for conventional chemotherapy.

However, many patients develop resistance. Two primary sources of resistance are the T790M Mutation and MET oncogene. However, as of 2010 there was no consensus of an accepted approach to combat resistance nor FDA approval of a specific combination. Preclinical results have been reported for AP26113 which targets the T790M mutation.

Epidermal growth factor receptor has been shown to interact with Androgen receptor, ARF4, Beta-catenin, Caveolin 1, Caveolin 3, Cbl gene, CBLB, CBLC, CDC25A, CRK, Decorin, Epidermal growth factor, GRB14, Grb2, Janus kinase 2, MUC1, NCK1, NCK2, PKC alpha, PLCG1, PLSCR1, PTPN1, PTPN11, PTPN6, SH2D3A, SH3KBP1, SHC1, SOS1, Src, STAT1, STAT3, STAT5A, Ubiquitin C, and Wiskott-Aldrich syndrome protein.

III. SYNDECAN PEPTIDES

A. Structure

The present invention contemplates the design, production and use of various syndecan peptides. The structural features of these peptides are as follows. First, the peptides have no more than about 75 consecutive residues of a syndecan (78-131 is 54 amino acids, and residues 87-131 is 45 residues). Thus, the term "a peptide having no more than 20 consecutive residues," even when including the term "comprising," cannot be understood to comprise a greater number of consecutive syndecan residues. Second, the peptides will contain the motifs responsible for interaction with EGFR. In general, the peptides will have, at a minimum, 40 consecutive residues of the syndecan, including 45 and 54 residues.

The overall length may be 45, 46, 47, 48, 49, 50, 55, 60, 65, 70, 75, 80, 85, 90 or 100 residues. Ranges of peptide length of 45-50 residues, 45-54 residues, 45-60 residues, 45-65 residues, 45-70, residues, 45-75 residues, 45-80 residues, 45-85 residues, 45-90 residues, and 45-100 residues are contemplated. The number of consecutive syndecan residues may be 45, 46, 47, 48, 49, 50, 51, 52, 53, 54, 55, 56, 57, 58, 59 or 60. Ranges of consecutive residues of 45-50 residues, 45-54 residues, 45-60 residues, 45-65 residues and 45-70 residues, 45-75, residues, 45-80 residues or 45-90 residues are contemplated.

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino- and/or carboxyl-terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the 20 standard amino acids that can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse syndecan peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

Another use of linkers in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge that physically constrains the peptide into its native α-helical shape. In addition to helping retain the native structure needed to interact with a target molecule, this conformation also provides stability against peptidases as well as cell-permeating properties. U.S. Pat. Nos. 7,192,713 and 7,183,059, describing this technology, are hereby incorporated by reference. See also Schafmeister et al., 2000.

D. Design, Variants and Analogs

Having identified structures in EGFR interaction with α6β4 integrins, the inventor also contemplates that variants of the sequences may be employed. For example, certain non-natural amino acids that satisfy the structural constraints of the sequences may be substituted without a loss, and perhaps with an improvement in, biological function. In addition, the present inventor also contemplates that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

As used herein, "molecular modeling" means quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

X-Ray Crystallography.

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy.

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the interaction of $\alpha 6\beta 4$ and EGFR. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

IV. THERAPIES

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intraperitoneal, or intravenous injection. Such compositions would normally be administered as pharmaceutically acceptable compositions, described supra. Of particular interest is direct intratumoral administration, perfusion of a tumor, or admininstration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional medium or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Cancer Types and Subjects

Cancer cells to which the methods of the present invention can be applied include generally any cell that expresses α6β4 integrin, and more particularly, that overexpresses α6β4 integrin. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

C. Treatment Methods

Peptides or analogs that inhibit α6β4 integrin engagement of EGFR are generally useful as anti-cancer therapeutics or prophylactics. They can be administered to mammalian subjects (e.g., human breast cancer patients) alone or in conjunction with other drugs and/or radiotherapy. The compounds can also be administered to subjects that are genetically and/or environmentally (due to, for example, physiological and/or environmental factors) susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke).

When the methods are applied to subjects with cancer, prior to administration of a compound, the cancer can optionally be tested for α6β4 integrin or EGFR expression or overexpression by methods known in the art. In this way, subjects can be identified as being susceptible to treatments according to the present invention. Such methods can be performed in vitro on cancer cells obtained from a subject. Alternatively, in vivo imaging techniques using, for example, radiolabeled antibodies specific for α6β4 integrin or EGFR can be performed.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 5-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Scarring and Other Pathologic Wound Healing

Wound healing is an essential process in maintaining health. However, in certain instances, wound healing can create health problems. These include hypertrophic scarring, keloid or dermoid formation, and exuberant granulation. These conditions are often supported by pathologic angiogenesis (discussed below). The present invention may be applied to address these conditions.

1. Keloids

A keloid is a type of scar which, depending on its maturity, is composed mainly of either type III (early) or type I (late) collagen. It is a result of an overgrowth of granulation tissue (collagen type 3) at the site of a healed skin injury which is then slowly replaced by collagen type 1. Keloids are firm, rubbery lesions or shiny, fibrous nodules, and can vary from pink to flesh-coloured or red to dark brown in colour. A keloid scar is benign, non-contagious, but sometimes accompanied by severe itchiness and pain, and changes in texture. In severe cases, it can affect movement of skin.

Keloids should not be confused with hypertrophic scars, which are raised scars that do not grow beyond the boundaries of the original wound. Keloids expand in claw-like growths over normal skin. They have the capability to hurt with a needle-like pain or to itch without warning, although the degree of sensation varies from patient to patient.

If the keloid becomes infected, it may ulcerate. Removing the scar is one treatment option; however, it may result in more severe consequences: the probability that the resulting surgery scar will also become a keloid is high, usually greater than 50%. Laser treatment has also been used with varying degrees of success.

Keloids form within scar tissue. Collagen, used in wound repair, tends to overgrow in this area, sometimes producing a lump many times larger than that of the original scar. Although they usually occur at the site of an injury, keloids can also arise spontaneously. They can occur at the site of a piercing and even from something as simple as a pimple or scratch. They can occur as a result of severe acne or chickenpox scarring, infection at a wound site, repeated trauma to an area, excessive skin tension during wound closure or a foreign body in a wound. Keloids can sometimes be sensitive to chlorine. Keloid scars can grow, if they appear at a younger age, because the body is still growing.

Histologically, keloids are fibrotic tumors characterized by a collection of atypical fibroblasts with excessive deposition of extracellular matrix components, especially collagen, fibronectin, elastin, and proteoglycans. Generally, keloids contain relatively acellular centers and thick, abundant collagen bundles that form nodules in the deep dermal portion of the lesion. Keloids present a therapeutic challenge that must be addressed, as these lesions can cause significant pain, pruritus (itching), and physical disfigurement. They may not improve in appearance over time and can limit mobility if located over a joint.

Keloids affect both sexes equally, although the incidence in young female patients has been reported to be higher than in young males, probably reflecting the greater frequency of earlobe piercing among women. There is a fifteen times higher frequency of occurrence in highly pigmented people. Persons of African descent are at increased risk of keloid occurrences.

The best treatment is prevention in patients with a known predisposition. This includes preventing unnecessary trauma or surgery (including ear piercing, elective mole removal), whenever possible. Any skin problems in predisposed individuals (e.g., acne, infections) should be treated as early as possible to minimize areas of inflammation.

Intra-Lesional Corticosteroids.

Intra-lesional corticosteroids are first-line therapy for most keloids. A systematic review found that up to 70 percent of patients respond to intra-lesional corticosteroid injection with flattening of keloids, although the recurrence rate is high in some studies (up to 50 percent at five years). While corticosteroids are one of the more common treatments, injections into and in close proximity to keloid tissue can be highly painful and can produce undesirable results in female patients, as per any other testosterone-based treatment.

Excision.

Scalpel excision may be indicated if injection therapy alone is unsuccessful or unlikely to result in significant improvement. Excision should be combined with preoperative, intraoperative, or postoperative triamcinolone or interferon injections. Recurrence rates from 45 to 100 percent have been reported in patients treated with excision alone; this falls to below 50 percent in patients treated with combination therapy.

Gel Sheeting.

Both hydrogel and silicone gel sheeting have been used for the treatment of symptoms (e.g., pain and itching) in patients with established keloids as well as for the management of evolving keloids and the prevention of keloids at the sites of new injuries. While the precise mechanism of action is still poorly understood, there is evidence that application of gel sheeting may reduce the incidence of abnormal scarring. A controlled study found significant changes in growth factor levels of fibronectin and IL-8 with application of hydrogel sheeting with respect to normal skin. Silicone sheeting was associated with changing growth factor levels of only fibronectin.

Cryosurgery.

Most useful in combination with other treatments for keloids. The major side effect is permanent hypopigmentation, which limits its use in people with darker skin.

Radiation Therapy.

Most studies, but not all, have found radiation therapy to be highly effective in reducing keloid recurrence, with improvement rates of 70 to 90 percent when administered after surgical excision. A small randomized trial of treatments after surgery found recurrences in two of sixteen earlobe keloids (13 percent) treated with radiation therapy and in four of twelve earlobe keloids (33 percent) treated with steroid injections. However, concern regarding the potential long-term risks (e.g., malignancy) associated with using radiation for an essentially benign disorder limits its utility in most patients. Only a few cases of malignancy that may have been associated with radiation therapy for keloids have been reported. Although causation cannot be confirmed in these cases, caution should still be used when prescribing radiation therapy for keloids, particularly when treating younger patients. Radiation therapy may occasionally be appropriate as treatment for keloids that are resistant to other therapies. In addition, radiation therapy may be indicated for lesions that are not amenable to resection.

Interferon Alpha.

Interferon alpha injections may reduce recurrence rates postoperatively. However, all currently available studies of interferon therapy suffer from methodologic problems, making an evidence-based recommendation regarding its use difficult.

Pulsed Dye Laser.

Pulsed dye laser treatment can be beneficial for keloids, and appears to induce keloid regression through suppression of keloid fibroblast proliferation, and induction of apoptosis and enzyme activity. Combination treatment with pulsed dye laser plus intralesional therapy with corticosteroids and/or fluorouracil may be superior to either approach alone.

2. Hypertrophic Scarring

Hypertrophic scars are a cutaneous condition characterized by deposits of excessive amounts of collagen which gives rise to a raised scar, but not to the degree observed with keloids. Like keloids, they form most often at the sites of pimples, body piercings, cuts and burns. They often contain nerves and blood vessels. They generally develop after thermal or traumatic injury that involves the deep layers of the dermis and express high levels of TGF-β.

When a normal wound heals the body produces new collagen fibers at a rate which balances the breakdown of old collagen. Hypertrophic scars are red and thick and may be itchy or painful. They do not extend beyond the boundary of the original wound but may continue to thicken for up to 6 months. They usually improve over the one or two years but may cause distress due to their appearance or the intensity of the itching, also restricting movement if they are located close to a joint.

Hypertrophic scars are more common in the young and people with darker skin. Some people have an inherited tendency to this type of scarring. It is not possible to completely prevent hypertrophic scars, so anyone who has suffered one should inform their doctor or surgeon if they need to have surgery. Scar Therapies are available which may speed up the process of change from a hypertrophic scar to a flatter, paler one. Scars do not occur in younger people as often as older people because their skin cells replicate more quickly and fill in the wound with normal skin tissue.

3. Proud Flesh

Granulation tissue is the perfused, fibrous connective tissue that replaces a fibrin clot in healing wounds. Granulation tissue typically grows from the base of a wound and is able to fill wounds of almost any size it heals. In addition, it is also found in ulcers like esophageal ulcer. However, when the granulation becomes uncontrolled, often resulting from improper wound care, a condition known as exuberant granulation or "proud flesh" results. The scar tissue, if untreated, may completely overtake the wound area. Caught early, the condition can be treated by topical or injected steroids, but more advanced cases require surgical intervention. Horses are subject to this disease, particularly in the legs. Also, some individuals of African decent have a genetic predisposition to exuberant scarring.

E. Pathologic Angiogenesis

Despite the abundancy of angiogenic factors present in different tissues, endothelial cell turnover in a healthy adult organism is remarkably low with a turnover in the order of thousands of days. The maintenance of endothelial quiescence is thought to be due to the presence of endogenous negative regulators. Moreover, positive and negative regulators often co-exist in tissues with extensive angiogenesis. These observations have led to the hypothesis that activation of the endothelium depends on a balance between these opposing regulators. If positive angiogenic factors dominate, the endothelium will be activated. Thus, the angiogenic process can be divided in an activation phase (initiation and progression of the angiogenic process) and a phase of resolution (termination and stabilization of the vessels). It is not yet clear whether the resolution phase is due to upregulation of endogenous inhibitors or exhaustion of positive regulators.

With respect to activated endothelium, an important distinction must be made between physiological and pathological settings. Although many positive and negative regulators operate in both, endothelial cell proliferation is tightly controlled in the former, whereas in the latter, the uncontrolled growth of microvessels may lead to several "angiogenic diseases" in different tissues, such as hemangiomas, psoriasis, Kaposi's sarcoma, ocular neovascularization, rheumatoid arthritis, endometriosis, atherosclerosis, tumor growth and metastasis, myocardial ischemia, peripheral ischemia, cerebral ischemia, wound healing, reconstructive surgery, and ulcer healing, and these may also be advantageously treated with the compositions of the present invention. Some of these are discussed in greater detail below.

Hemangiomas are angiogenic diseases, characterized by the proliferation of capillary endothelium with accumulation of mast cells, fibroblasts and macrophages. They represent the most frequent tumors of infancy, occurring more frequently in females than males (3:1 ratio). Hemangiomas are characterized by rapid neonatal growth (proliferating phase). By the age of 6 to 10 months, the hemangioma's growth rate becomes proportional to the growth rate of the child, followed by a very slow regression for the next 5 to 8 years (involuting phase). Most hemangiomas occur as single tumors whereas about 20% of the affected infants have multiple tumors, which may appear at any body site. Approximately 5% produce life-, sight-, or limb-threatening complications, with high mortality rates. The pathogenesis of hemangiomas has not yet been elucidated. However, several immunohistochemical studies have provided insight into the histopathology of these lesions. In particular, proliferating hemangiomas express high levels of proliferating cell nuclear antigen (PCNA, a marker for cells in the S phase), type IV collagenase, VEGF and FGF-2. During the involuting phase of hemangiomas, expression of these angiogenic factors decreases. Furthermore, urinary levels of FGF-2 are elevated during the proliferating phase of hemangioma, but become normal during involution or after therapy with IFN-α.

Other proliferative disorders of the skin include psoriasis and Kaposi's sarcoma. Hypervascular psoriatic lesions express high levels of the angiogenic inducer IL-8, whereas the expression of the endogenous inhibitor TSP-1 is decreased. Kaposi's sarcoma (KS) is the most common tumor associated with human immunodeficiency virus (HIV) infection and is in this setting almost always associated with human herpes virus 8 (HHV-8) infection. Typical features of KS are proliferating spindle-shaped cells, considered to be the tumor cells and endothelial cells forming blood vessels. KS is a cytokine-mediated disease, highly responsive to different inflammatory mediators like IL-1β, TNF-α and IFN-γ and angiogenic factors. In particular, FGF-2 was found to synergize with HIV-tat to promote angiogenesis and KS development. Finally, growth of KS, both in vitro and in vivo, could be blocked by an antisense oligonucleotide targeting FGF-2.

Diabetic retinopathy is the leading cause of blindness in the working population, but ocular neovascularization can also occur upon exposure of preterm babies to oxygen. It is assumed that both forms are induced by hypoxia in the retina. Elevated levels of the hypoxia-inducible angiogenic factor VEGF were detected in the aqueous and vitreous of eyes with proliferative retinopathy.

Excessive production of angiogenic factors from infiltrating macrophages, immune cells or inflammatory cells may also trigger the formation of pannus, an extensively vascularized tissue that invades and destroys the cartilage, as seen in rheumatoid arthritis. Moreover, uncontrolled angiogenesis may underlie various female reproductive disorders, such as prolonged menstrual bleeding or infertility, and excessive endothelial cell proliferation has been observed in the endometrium of women with endometriosis.

Angiogenesis also contributes to atherosclerosis, a major cause of death of Western populations. Atherosclerosis is the main cause of heart attack. The walls of the coronary artery are normally free of microvessels except in the atherosclerotic plaques, where there are dense networks of capillaries, known as the vasa vasorum. These fragile microvessels can cause hemorrhages, leading to blood clotting, with a subsequent decreased blood flow to the heart muscle and heart attack. Finally, angiogenesis is thought to be indispensable for solid tumor growth and metastasis.

V. COMBINATION THERAPIES

Tumor cell resistance to DNA damaging agents represents a major problem in clinical oncology. One goal of current cancer research is to find ways to improve the efficacy of chemo- and radiotherapy. One way is by combining such traditional therapies with gene therapy. In the context of the present invention, it is contemplated that syndecan peptide therapy could be used similarly in conjunction with chemotherapeutic, radiotherapeutic, or immunotherapuetic intervention.

To kill cells, inhibit cell growth, inhibit metastasis, inhibit angiogenesis or otherwise reverse or reduce the malignant phenotype of tumor cells, using the methods and compositions of the present invention, one would generally contact a target cell with a syndecan peptide and at least one other therapy. These therapies would be provided in a combined amount effective to kill or inhibit proliferation of the cell. This process may involve contacting the cells with the agents/therapies at the same time. This may be achieved by contacting the cell with a single composition or pharmacological formulation that includes both agents, or by contacting the cell with two distinct compositions or formulations, at the same time, wherein one composition includes the syndecan peptide and the other includes the agent.

Alternatively, the syndecan treatment may precede or follow the other treatment by intervals ranging from minutes to weeks. In embodiments where the other treatment and the syndecan peptide are applied separately to the cell, one would generally ensure that a significant period of time did not expire between the time of each delivery, such that the therapies would still be able to exert an advantageously combined effect on the cell. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) pass between the respective administrations.

It also is conceivable that more than one administration of either the syndecan peptide or the other therapy will be desired. Various combinations may be employed, where the syndecan peptide is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated. Again, to achieve cell killing, both therapies are delivered to a cell in a combined amount effective to kill the cell.

Agents or factors suitable for use in a combined therapy include any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition.

Various classes of chemotherapeutic agents are comtemplated for use in combination with peptides of the present invention. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with peptides, as described above.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include Adriamycin, also known as Doxorubicin, Etoposide, Verapamil, Podophyllotoxin, and the like. Widely used in a clinical setting for the treatment of neoplasms, these compounds are administered through bolus injections intravenously at doses ranging from 25-75 mg/m$^2$ at 21 day intervals for Doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventor proposes that the local or regional delivery of syndecan peptides to patients with cancer will be a very efficient method for treating the clinical disease. Similarly, the chemo- or radiotherapy may be directed to a particular, affected region of the subject's body. Alternatively, regional or systemic delivery of expression construct and/or the agent may be appropriate in certain circumstances, for example, where extensive metastasis has occurred.

Combination with immunotherapy, hormone therapy, toxin therapy and surgery also is contemplated. In particular, one may employ targeted therapies such as Avastin, Erbitux, Gleevec, Herceptin and Rituxan.

It also should be pointed out that any of the foregoing therapies may prove useful by themselves in treating cancer.

VI. EXAMPLES

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Antibodies and Reagents.

Antibodies used were mouse mAb 3E1 and P1B5 (Chemicon, Temecula, Calif.) to β4 and β1 integrin extracellular domains, respectively; rabbit polyclonal antibody Ab1922 (Millipore, Billerica, Mass.) to the β4 cytoplasmic domain; rabbit antibody BM165 (kindly provided by Dr. Peter Marinkovich, Stanford University, CA) against laminin α3 chain. The inventors used mouse mAbs B-A38 (Accurate Chemical and Scientific, Westbury, N.Y.) and 150.9 (University of Alabama Hybridoma Facility) to human Sdc1 and human Sdc4, respectively and rat mAb 281.2 (65) or KY 8.2 (66) against mouse Sdc1 or mouse Sdc4, respectively. HER2 was recognized by anti-c-ErbB-2 Ab-15 (clone 3B5) (Fisher). EGFR-specific antibody (sc-03-G) was from Santa Cruz.

Dulbecco's modified Eagles medium (DMEM) and rhodamine-conjugated phalloidin were from Invitrogen (Grand Island, N.Y.); Glutathione-conjugated Sepharose beads were from GE Healthcare Biosciences Corp (Piscataway, N.J.); Human recombinant epidermal growth factor (rhEGF) was from Sigma Aldrich (St. Louis, Mo.); ErbB2 inhibitor (AG825) was from Chemicon; EGFR inhibitor (Iressa) was kindly provided by Dr. Deric Wheeler (University of Wisconsin, WI). Human Sdc1 siRNA (target sequence GGAGGAATTCTATGCCTGA; SEQ ID NO. 2) and human Sdc4 siRNA (target sequence CAGGAATCTGATGACTTTGAG; SEQ ID NO. 3) were from Ambion.

Peptides comprising the $SSTN_{EGFR}$ site in the Sdc4 extracellular domain were synthesized by NeoBioLab, Inc. (Cambridge, Mass.). The activity of $SSTN_{EGFR}$ was compared to other SSTN peptides being developed in the laboratory. These include $SSTN_{HER2}$ (also obtained from NeoBioLab, Inc.) and $SSTN_{IGF1R}$, obtained from Genscript USA, Inc., (Piscataway, N.J.).

Plasmid Constructs.

The cDNAs of all syndecans were inserted into the pcDNA3 vector using restriction sites engineered into the 5' ends of the primers used to amplify the syndecan fragments. Deletion of the C2 domain of mouse Sdc1 and Sdc4 in pcDNA3 vector was made by inserting a stop codon before the EFYA sequence by using the Quikchange Site Directed Mutagenesis Kit (Stratagene, La Jolla, Calif.). The cDNA of human integrin β4 were inserted into pcDNA vector. The cDNA of integrin β4 fragment encoding amino acids 1677-1752 was inserted into pTRC-His A vector; site mutations and deletions were generated by using the Quikchange Site Directed Mutagenesis Kit.

Cell Culture and Transfection.

Human HaCat keratinocytes, Head and Neck squamous carcinoma cell lines, and BT474 and SKBr3 mammary carcinoma cells were grown in DMEM, supplemented with 10% calf serum or 10% fetal bovine serum (Hyclone Laboratories, Logan, Utah), 4 mM L-glutamine (Sigma), and 100 units/ml penicillin and 100 g/ml streptomycin (Invitrogen) at 37° C. and 92.5% air, 7.5% CO2. MCF10A mammary epithelial cells were grown in DMEM F12 50/50 plus 15 mM Hepes, L-glutamine, 5% horse serum, 10 μg/ml insulin, 0.5 μg/ml hydrocortisone, and 0.02 μg/ml EGF. Cells were transfected with syndecan or integrin β4 constructs in pcDNA3 using Lipofectamine PLUS (Invitrogen) and 10 μg of plasmid by following the manufacturer's instructions. Stable populations were selected in 1.0 mg/ml G418 (Invitrogen).

siRNA Treatment and Flow Cytometry.

Oligos of siRNAs specific for human Sdc1 or Sdc4 were used as described previously (Beauvais et al., 2004). To measure cell surface syndecan expression, suspended cells were incubated for 1 h on ice with 1 μg of primary antibody per $3 \times 10^5$ cells and then washed and counterstained with Alexa-488-conjugated secondary antibodies and scanned on a FACSCalibur bench top cytometer. Cell scatter and propidium iodide staining profiles were used to gate live, single-cell events for data analysis (Beauvais et al., 2004; Beauvais et al., 2006).

Fusion Protein Expression and Purification.

6×His-β4CD1677-1752 fusion protein was expressed in E. coli by IPTG induction and purified on Ni-NTA beads following cell lysis in 100 mM NaH2PO4, 10 mM Tris base and 8 M urea, (8.0). GST-S1CD or GST-S4CD fusion proteins and truncated versions were expressed in E. coli by IPTG induced and purified on glutathione-sepharose beads following cell lysis in 150 mM NaCl, 20 mM sodium phosphate (pH 7.4) and 1% triton X-100.

Wound Healing Assay.

HaCat or MCF10A cells grown to confluence on 48 well-plates were starved for 6 hr by serum deprivation followed by introduction of a scratch wound in the monolayer using 200 μl pipette tip. To induce haptotactic migration that depends on Sdc1, cells were cultured an additional 12 hr in DMEM containing mAb 3E1 (10 μg/ml), goat anti-mouse IgG (50 μg/ml) and 3 μM LPA. To cause EGF-stimulated chemotactic migration that depends on Sdc4, cells were stimulated with EGF (10 ng/ml). Images were acquired using a PlanApo 20 (0.75 numerical aperture) objective and a Photometrics CoolSnap ES camera on a Nikon Eclipse TE2000U microscopy system and wound closure quantified.

Immunoprecipitation.

Immunoprecipitations were carried out as described previously (Beauvais et al., 2004; Beauvais et al., 2006). Cells were washed once with washing buffer (50 mM Hepes, 50 mM NaCl and 10 mM EDTA, pH 7.4) and lysed for 20 min on ice in 1% Triton X-100 containing a 1:1000 dilution of protease inhibitor mixture set III (Calbiochem) in washing buffer. Cell debris was removed by centrifugation at 20,000 g for 15 min at 4° C. Lysates or 6×His-tagged β4 cytoplasmic domain (amino acids 1677-1752) were incubated at 4° C. overnight with 100 μl Glutathione Sepharose 4B beads (50% in IP wash buffer), GST-S4CD or GST-S1CD in present or absent of different peptides. Samples were resolved by electrophoresis under reduced conditions on a 15% Laemmli gel, transferred to Immobilon P, and probed with primary antibody followed by an alkaline phosphatase-conjugated secondary antibody. Visualization of immune-reactive bands was performed using ECF reagent (GE Healthcare) and scanned on a Typhoon Trio Variable Mode Imager (GE-Healthcare) in blue fluorescence.

Apoptosis Assay.

Cells ($5 \times 10^4$/well in a 24-well plate) were treated with GST fusion protein (GST, GST-S1ED or GST-S4ED) or synstatin peptides ranging in concentration from 1 to 30 μM. Cell death was observed by Cell Tilter-GLO Cell Viability Assay (Promega).

Example 2

Results

Figure 2:
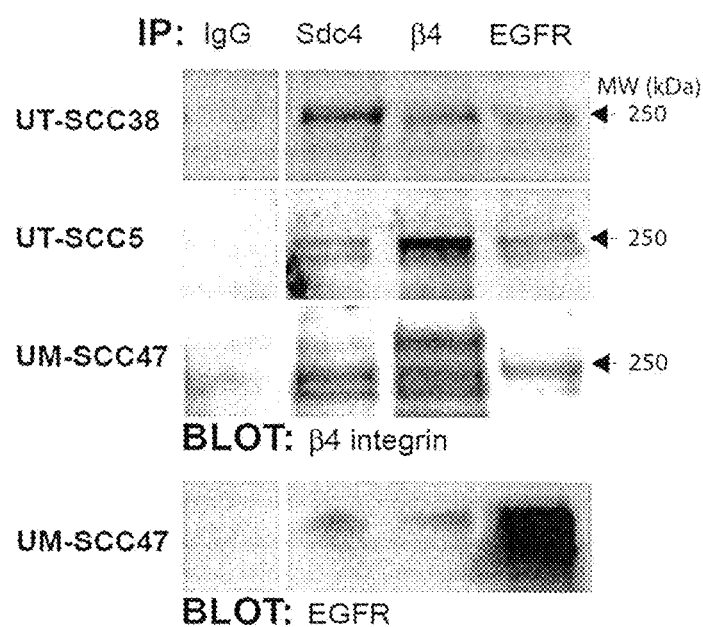
FIG. 2. Co-immunoprecipitation of α6β4 together with Sdc4 and EGFR from HNSCC cells. Sdc4, β4 integrin, and EGFR were immunoprecipitated from lysates of HNSCC cells and probed on Western blots for β4 integrin or for EGFR (UM-SCC47 cells only). Note that the integrin and EGFR co-precipitate with Sdc4 and with each other. Note that the integrin subunit is sometimes observed as multiple bands, possibly due to glycosylation differences. (Intervening lanes separating the IgG control and Sdc4 were removed for clarity of presentation).
Figure 3:
FIG. 3. Sdc4-coupled EGFR/α6β4 complex in MCF10 and BT474 human mammary cells. Antibodies to Sdc4 or Sdc1 (as a control), β4 integrin, or EGFR were used to immunoprecipitate the receptors from lysates of MCF10A normal mammary epithelial cells or BT474 (HER2+) breast carcinoma grown in serum. Blots were then probed for co-precipitation with EGFR.

The inventor initially discovered using a yeast-two hybrid assay that all four syndecans engage the cytoplasmic domain of the β4 integrin, relying in part on the conserved C2 domain at their extreme C-terminus (Wang et al., 2010) (see FIGS. 5A-B). Extending this to functional studies, the inventor found find that although all four syndecans engage the integrin cytoplasmic domain, there is apparent specificity in which syndecan associates with the integrin when it is complexed with different receptor tyrosine kinases. Focusing on syndecan-4 (Sdc4), he found that Sdc4 associates with α6β4 integrin and EGFR. Immunoprecipitation of either Sdc4, the β4 integrin subunit (which precipitates the α6β4 integrin), or EGFR causes precipitation of EGFR from lysates of head and neck squamous carcinoma (HNSCC) cells (FIG. 2) and from breast epithelial cells, including the normal MCF10A cells or the breast carcinoma BT474 (FIG. 3). The inventor found that this is specific for Sdc4, as immunoprecipitation of Sdc1 (as a comparison) co-precipitates the integrin (not shown), but fails to co-precipitate EGFR (shown for the breast epithelial cells in FIG. 3).

It is known that keratinocyte migration depends on the α6β4 and mimics a normal skin wound healing mechanism that occurs in response to EGF. The α6β4 and α3β1 integrins collaborate to deposit laminin (LN332), which is the ligand recognized by these two integrins, and then use the integrins for the signaling mechanism necessary for migration on this substratum (Russell et al., 2003; Sehgal et al., 2006). Testing the migration of human HaCat keratinocytes in a scratch wound assay in which EGF stimulates wound closure, the inventor found that blocking either of these two integrins, or blocking their binding site on LN332, disrupts wound closure, as expected (FIG. 4A). The inventor also found that migration is not inhibited by 10 μM tyrphostin AG825, which blocks the kinase activity of the EGFR family member HER2 but does not block EGFR; in contrast, the EGFR-specific kinase inhibitor Iressa (getintinib) used at 1 μM, which fails to block HER2 but inhibits EGFR, does block wound closure, confirming that the signaling mechanism leading to cell migration depends on the EGFR (FIG. 4A). Next, the inventor silenced the expression of the two main syndecans expressed on the HaCat cells—Sdc1 and Sdc4. He found that silencing human Sdc1 expression has only a minimal effect on cell migration, an effect that can be rescued by expression of mouse Sdc1 (which is not affected by the siRNA used to silence the human form), but cannot be rescued by Sdc1 lacking its C2 region (mSdc1ΔC2) necessary for engaging the α6β4 integrin cytoplasmic domain. This cytoplasmic domain engagement by the syndecan is necessary for phosphorylation of the integrin by the HER2 kinase (Wang et al., 2010), suggesting that Sdc1 engagement with the integrin may have some role, although a minor one, in the migration mechanism. In contrast, silencing Sdc4 expression reduces migration to that of non-stimulated cells (e.g., no EGF addition). This migration is rescued by expression of mouse Sdc4, but cannot be rescued by $Sdc4^{\Delta C2}$ that fails to engage the β4 integrin cytoplasmic domain (FIG. 4B). This implicates Sdc4 and its interaction with the integrin during EGF stimulated migration, likely reflecting the association observed via Immunoprecipitation in FIGS. 2 and 3.

Figure 7:
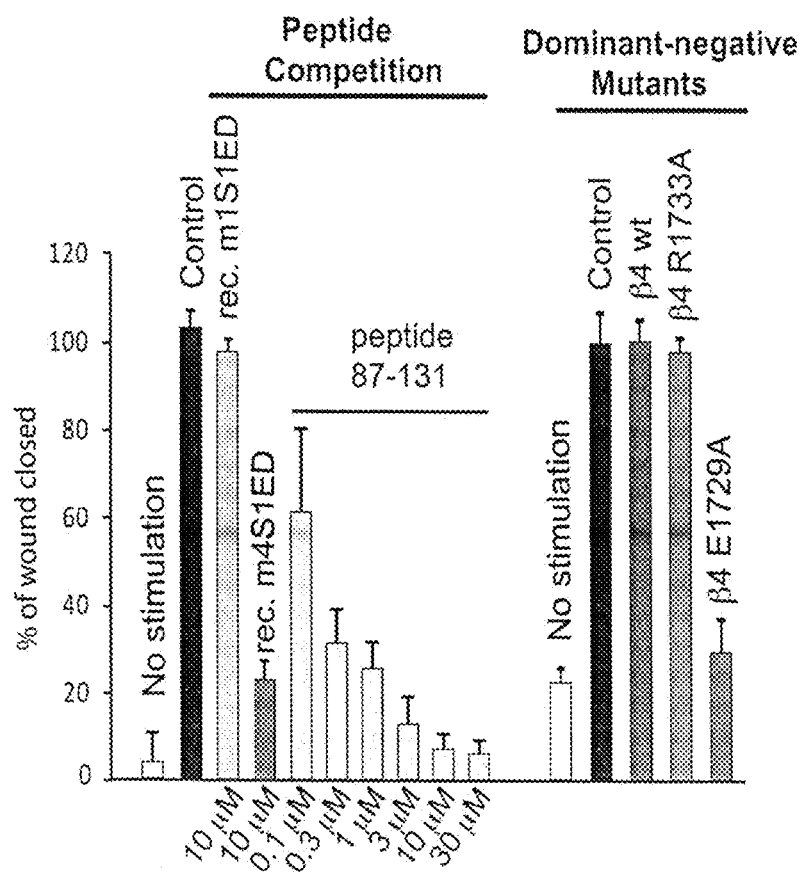
FIG. 7. EGFR-dependent migration of MCF10A mammary epithelial cells is blocked by recombinant Sdc4 ectodomain, a peptide representing the active site in Sdc4 (amino acids 87-131) or a Sdc4-specific dominant negative α6β4 integrin. Migration of human MCF10A mammary epithelial cells in response to EGF (10 ng/ml) is tested in 12 hr scratch wound closure assays. Peptide competition: Sdc4 ectodomain (GST-S4ED) fusion protein blocks EGF-stimulated migration by 80% at 10 µM, whereas GST-S1ED (from Sdc1, used as a control) has no effect. Using this assay to test shorter Sdc4 peptides, the inventor found that a synthetic peptide comprising amino acids 87-131 in the Sdc4 ectodomain is at least as effective as the entire ectodomain, displaying an $IC_{50}$ of 0.1-0.3 µM. Dominant-negative mutants: A β4 cytoplasmic domain mutant ($β4^{E1729A}$) that cannot engage Sdc4 blocks EGF-stimulated chemotaxis, thus disrupting the activity of the endogenous β4 integrin (dominant negative mutant). A β4 integrin mutant ($β4^{R1733A}$) that cannot engage Sdc1 but still binds Sdc4 has no effect (used as a control).
Figure 9A:
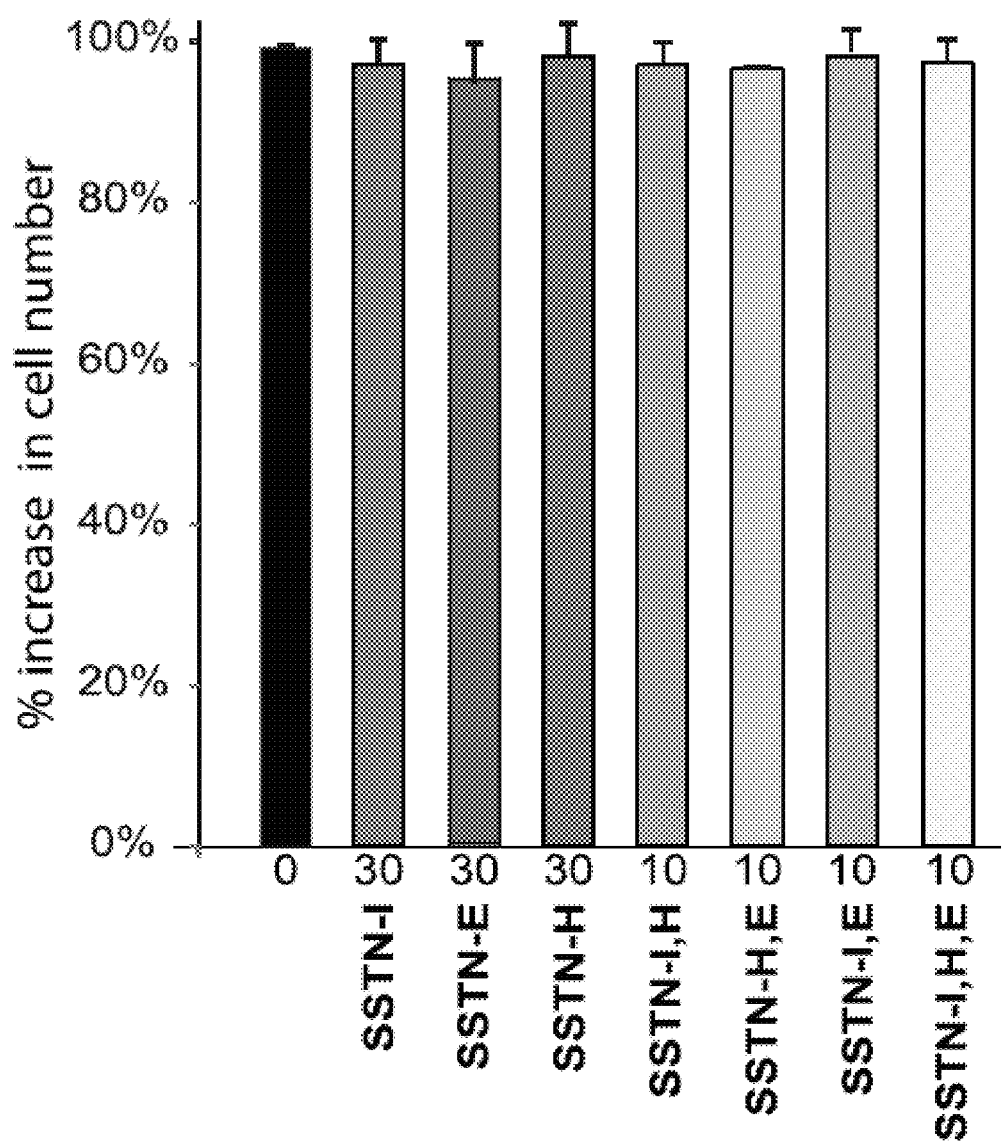
FIGS. 9A-F. SSTN treatment of normal (nontransformed) epithelial cells versus carcinoma (transformed) cells. Cells are plated for one day, then treated with either 3-30 µM $SSTN_{IGF1R}$ (SSTN-I), 3-30 µM $SSTN_{EGFR}$ (SSTN-E), 3-30 µM $SSTN_{HER2}$ (SSTN-H) or combinations of the three peptides, each at 10 µM to test their additive effect. Total cell number (a combination of cell proliferation and cell death) is measured using the CellTiterGLO assay (Promega) and is plotted as a percentage of untreated cells after either 4 or 7 days of treatment (less than 0% demonstrates cell death). The treatment times are chosen to reflect only modest effects of the peptides used singly, so that the more pronounced effect of peptides used in combination can still be observed. Treatment for longer times leads to significant cell death observed even with single peptides alone.
Figure 9B:
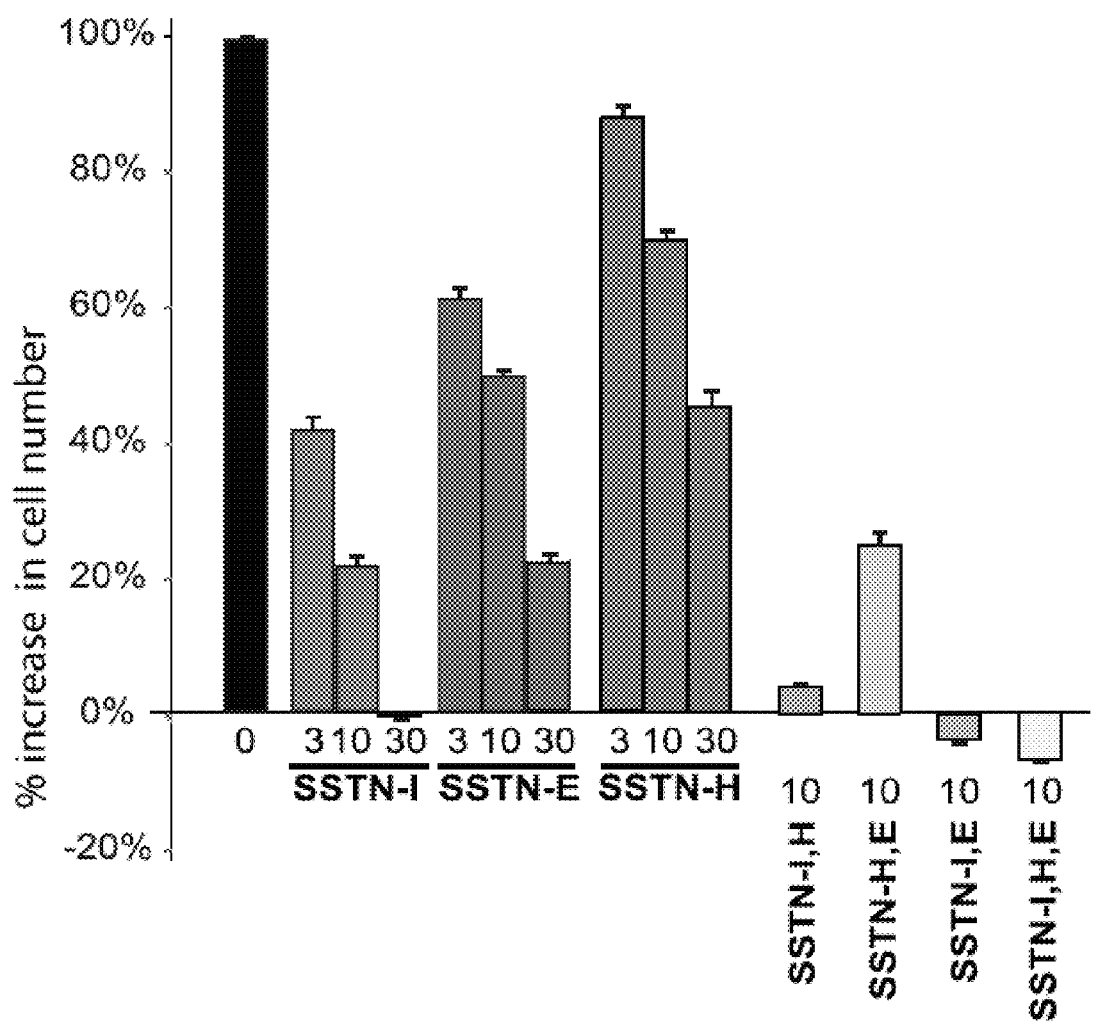
Figure 9C:
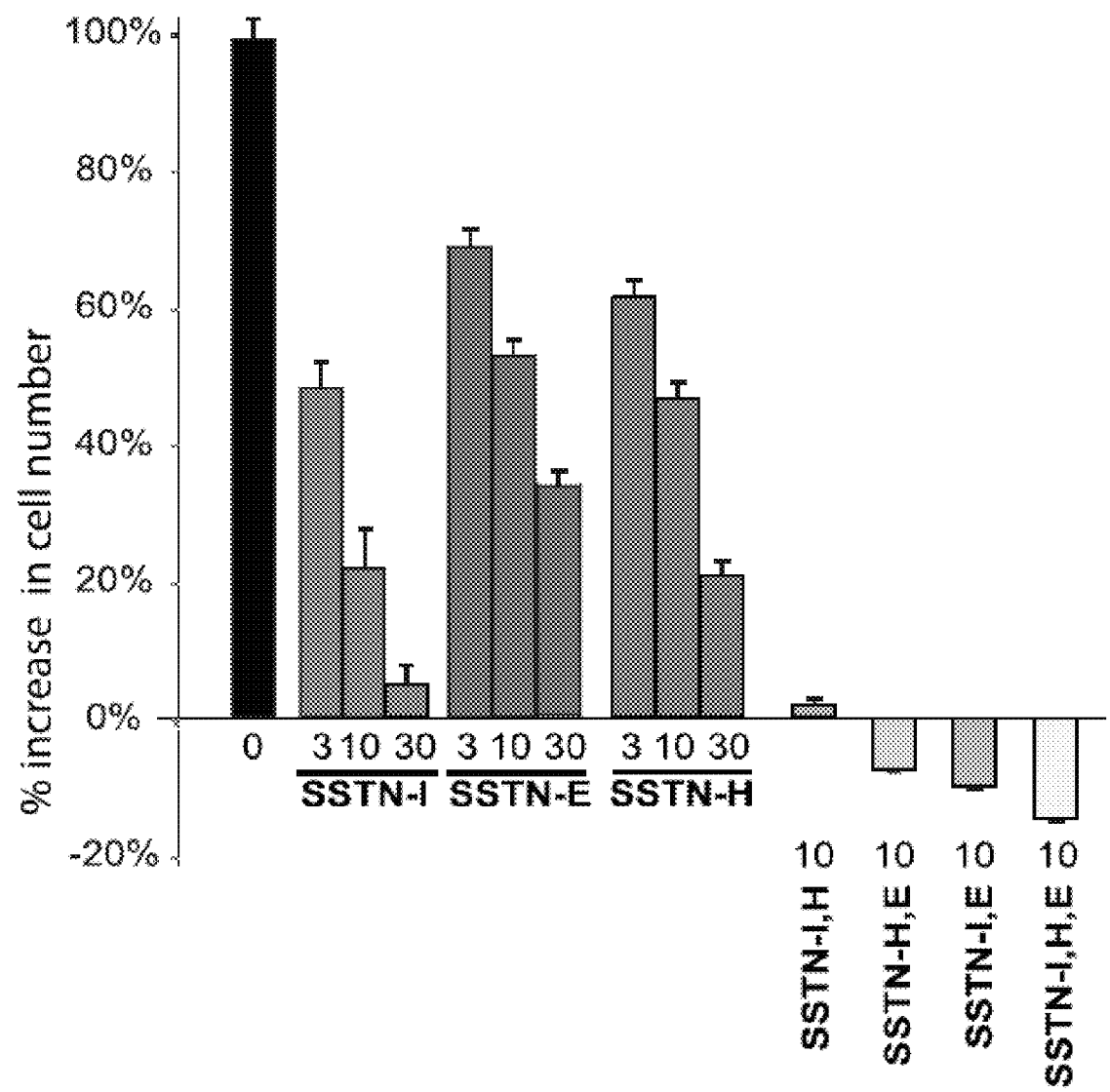
Figure 9D:
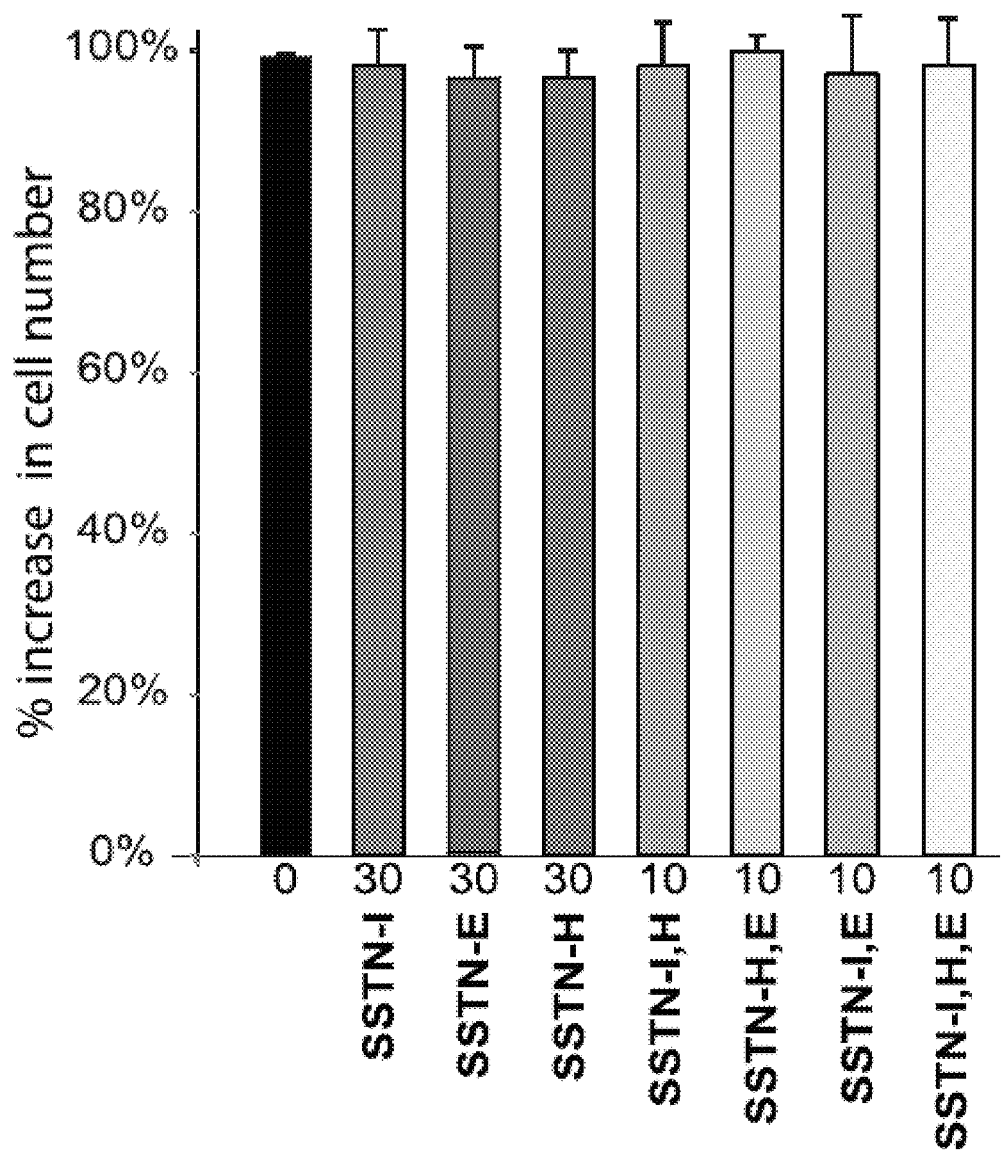
Figure 9E:
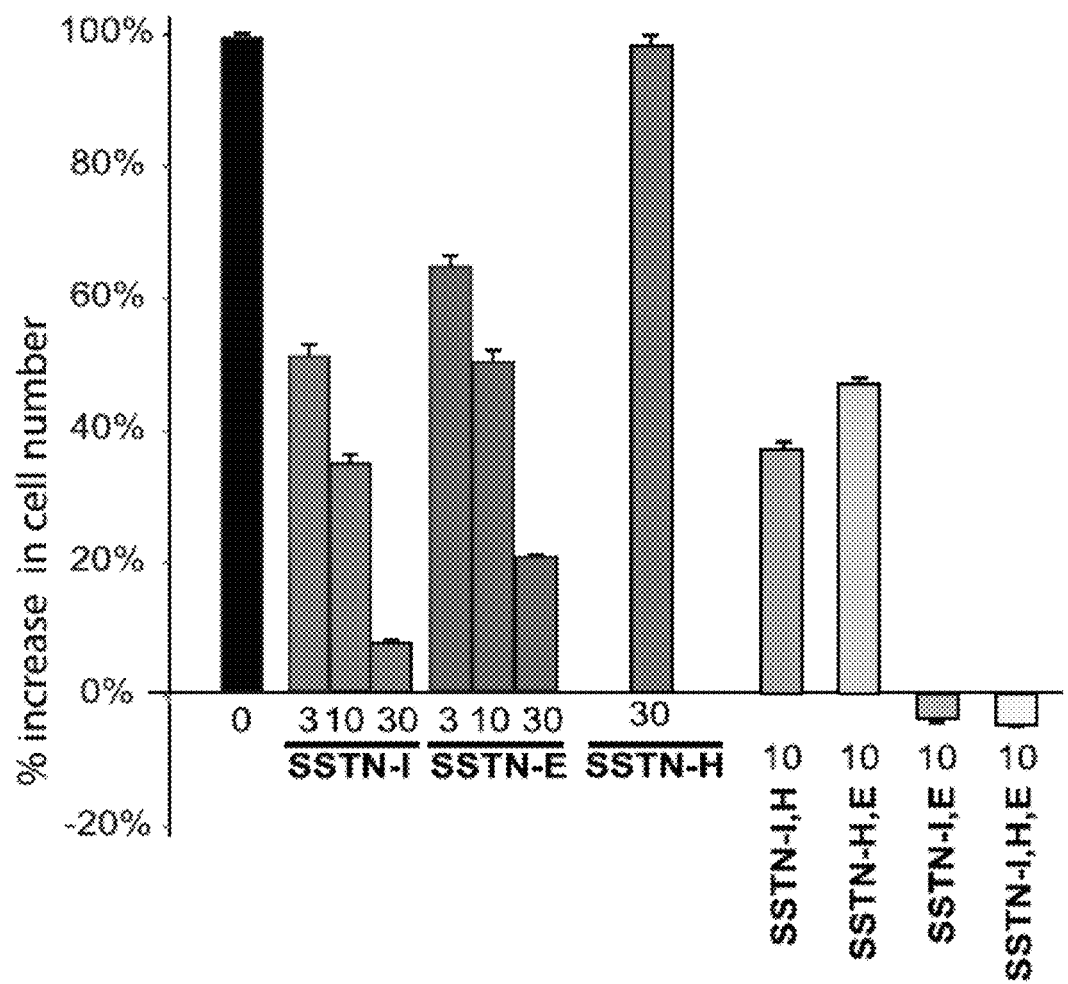
Figure 9F:
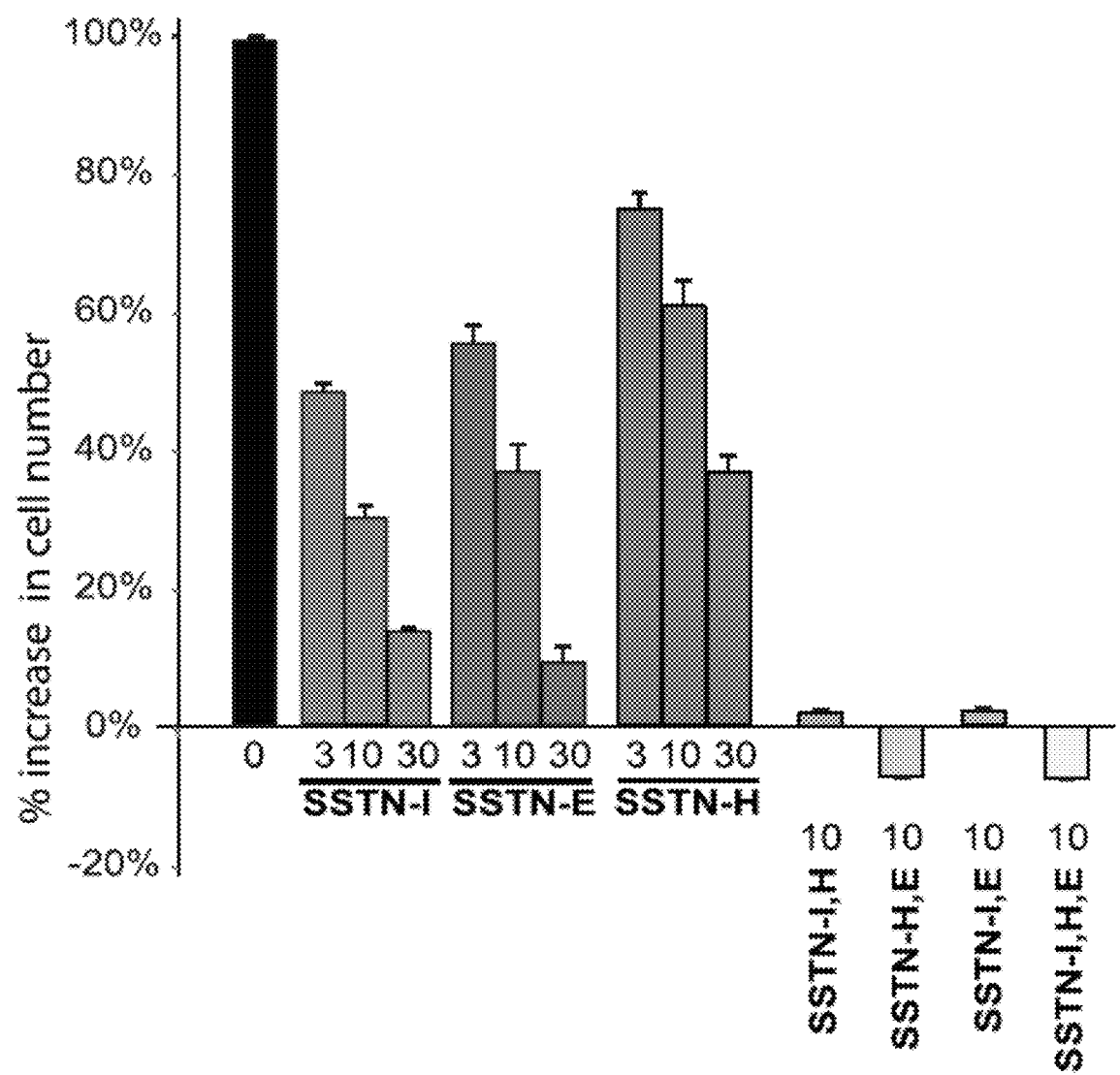

Further comparing the integrin association with either Sdc1 or Sdc4, the inventor found that the syndecans rely on distinct and highly specific cytoplasmic and extracellular motifs to assemble these receptor complexes and that these specific interactions dictate whether the mechanism will rely on Sdc1 and HER2 kinase to cause haptotactic migration, or Sdc4 and EGFR kinase for EGF-stimulated chemotaxis. Binding motifs near the C-terminus of both Sdc1 and Sdc4 engage binding sites near the C-terminus of the β4 integrin, but these binding sites are distinct for the two syndecans (FIGS. 5A-B). At least one amino acid within the EFYA sequence (the C2 region) that both syndecans share at their extreme C-terminus seems to be required (explaining why the ΔC2 mutants fail to engage the integrin), but additional amino acids in the V region that is not shared between the two receptors also have a role. In the β4 integrin, the binding site for both syndecans is within the last 24 amino acids at its C-terminus, as deletion of this region abolishes binding for both syndecans. The inventor found that E1729 in the β4 cytoplasmic domain is highly specific for Sdc4, as its mutation to alanine ($β4^{E1729A}$ mutant) reduces its affinity for Sdc4 without affecting its affinity for Sdc1. Conversely, R1733 is highly specific for Sdc1, as its mutation to alanine ($β4^{R1733A}$ mutant) reduces its affinity for Sdc1 but not Sdc4. These two mutants act as dominant negative mutants when expressed in cells; that is, the E1729A mutant competes for the Sdc4-coupled mechanism and blocks it, whereas the R1733A mutant competes for and blocks the Sdc1-coupled mechanism. When expressed in HaCat or MCF10A cells that appear to rely on Sdc4 for EGF-stimulated chemotaxis (based on siRNA silencing of Sdc4), the inventor found that the $β4^{E1729A}$ mutant that disrupts the Sdc4-specific signaling mechanism blocks the migratory response of the cells to EGF; In contrast, the Sdc1-specific $β4^{R1733A}$ mutant does not block the response, providing additional support for the hypothesis that Sdc4 and its coupling to the α6β4 integrin is necessary for this EGF-mediated signaling (FIG. 7).

The inventor's prior work has shown that Sdc1 contains a site in its extracellular domain to capture the αvβ3 or αvβ5 integrin and the insulin-like growth factor-1 receptor (IGF1-R) (Beauvais et al., 2009; Beauvais & Rapraeger, 2010). This capture is necessary for these receptors to cause carcinoma cell migration and for endothelial cells to undergo angiogenesis. This work acts as a model for the Sdc4-EGFR signaling mechanism and suggests that Sdc4 may also rely on a specific site in its extracellular domain to capture the α6β4 integrin and/or EGFR necessary for EGF-stimulated chemotaxis, in addition to its specific interaction with the cytoplasmic domain of the α6β4 integrin. To test this, the inventor swapped the extracellular domain of Sdc1, which does not appear to participate in EGF chemotaxis, with that of Sdc4, and then tested the ability of these chimeras to co-precipitate with EGFR from HaCat keratinocytes. He found that Sdc1 bearing the ectodomain of Sdc4 now assembles with EGFR (FIG. 6A), whereas Sdc4 displaying the Sdc1 ectodomain has lost this ability. Next, demonstrating that this capture is dependent solely on the syndecan ectodomain, the inventor found that beads coated with recombinant Sdc4 ectodomain (GST-S4ED) captures EGFR from HaCat cell lysates (FIG. 6B). Re-probing the blot shows that α6β4 integrin is also captured (data not shown), suggesting it is the α6β4 integrin/EGFR together that are captured via an interaction site in the Sdc4 ectodomain. In contrast, GST-S1ED fails to capture EGFR, but does capture HER2, coinciding with the role of Sdc1 in α6β4/HER2-stimulated haptotaxis (Wang et al., 2010).

These findings suggest that the recombinant Sdc4 extracellular domain contains a specific interaction site necessary for capture of EGFR and/or the α6β4 integrin, and that a peptide representing this site might serve to disrupt the α6β4/EGFR signaling mechanism. Indeed, the inventor found that competition with the entire recombinant S4ED disrupts the EGF-stimulated chemotaxis of MCF10A human mammary epithelial cells (FIG. 7) or HaCat keratinocytes (data not shown) with an $IC_{50}$ of 0.1-0.3 μM (see summary in FIGS. 8A-C). Both mouse and human proteins compete with the same affinity. In contrast, the ectodomain of Sdc1 (S1ED) fails to display any inhibitory effect. The inventor next used this assay to further truncate the recombinant S4ED protein to find the smallest peptide that retains full inhibitory activity and which would be a new synstatin for potential therapeutic use (e.g., $SSTN_{EGFR}$). The mature human Sdc4 ectodomain (e.g., lacking its signal peptide) is 127 amino acids in length. The inventor found that any truncated version of this protein that retains the sequence between amino acids 87-131 of human Sdc4 retains full competitive activity (FIG. 8A), suggesting that the active motif is contained within this 45 amino acid sequence. Indeed, a peptide containing these amino acids, which is called $SSTN_{EGFR}$, blocks EGF-stimulated MCF10A cell migration with an $IC_{50}$ of 0.1-0.3 mM (FIG. 7). There are several regions of conservation within this sequence (FIG.

8B), especially an NxIP motif at the N-terminus of the competitive peptide, an internal NEV motif, and an SNK-VSM motif at the C-terminal end. Mutation of NxIP to NxAP reduces the competitive activity 10-fold, either in the recombinant S4ED fusion protein (FIG. 8A) or in the synthetic peptide comprising amino acids 87-131 (FIG. 8C). Mutation of the NEV motif to AAA appears to have little if any effect (FIG. 8A). But truncation of the SNKVSM motif causes over a 100-fold loss of activity (FIG. 8C). Thus, the 87-131 sequence comprises a nearly minimal peptide that retains full competitive activity. In addition to the NxIP and SNKVSM (SEQ ID NO: 6) motifs that define its N- and C-terminal ends, an internal VPTEPKxLEE (SEQ ID NO: 7) motif conserved in mammals is also important, as a 10-fold loss of activity is observed if this sequence is mutated to AAAAAAAAAA (SEQ ID NO: 8) in the synthetic SST-$N_{EGFR}$ peptide (FIG. 8C).

Signaling from growth factor receptors and integrins is often critical not only for cell migration and tumor cell invasion, but also for cell proliferation and survival. Thus, the inventor has tested the potential role of the Sdc4-coupled α6β4/EGFR mechanism on the growth and survival of either normal epithelial or carcinoma cells using the $SSTN_{EGFR}$ peptide. The inventor tested the peptide on the HaCat keratinocytes that he has used for migration studies, an example of a normal stratified epithelium, and against the MCF10A cells that he has also used in migration studies, an example of a normal human breast epithelium. He found that although $SSTN_{EGFR}$ blocks EGF-stimulated chemotaxis of these normal cells, it has no effect on their growth or survival when used at concentrations as high as 30 µM (FIGS. 9A-F). The inventor also tested the peptide in combination with other SSTN peptides that he developed: $SSTN_{IGF1R}$ that targets a Sdc1-αvβ3 integrin-IGF1R receptor complex, and $SSTN_{HER2}$, that targets a Sdc1-α6β4 integrin-HER2 kinase complex. None of these SSTNs or SSTN combinations affect the normal epithelial cells. In contrast, however, $SSTN_{EGFR}$ and the other SSTNs do target growth/survival mechanisms in the carcinoma cells. This includes the UM-SCC47 and SCC25 squamous carcinoma of the human tongue—tumors that are derived from stratified epithelia as are the normal HaCat keratinocytes—and MDA-MB-468 and SKBr3 human breast carcinoma cells, representative of tumors arising from breast epithelium. These experiments represent relatively short treatment times (4 or 7 days). Nonetheless, cell death is observed in those cases where peptide combinations are used (shown by a reduction in cell number to fewer cells than the number present at the start of the assay). Thus, remarkably, tumor cells but not normal epithelial cells rely on the Sdc4-α6β4-EGFR complex for their growth and survival, and $SSTN_{EGFR}$ effectively blocks this dependence, especially when used in combination with other SSTN peptides.

Figure 10:
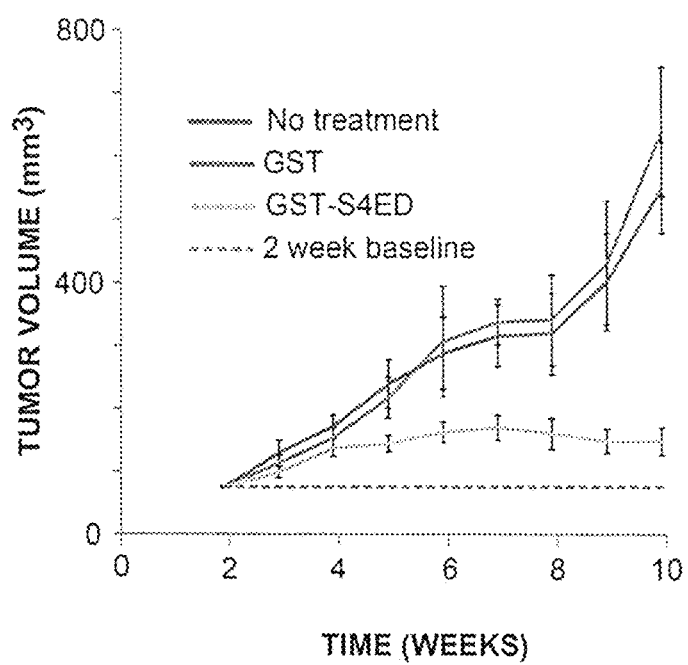
FIG. 10. S4ED blocks MDA-MB-468 breast carcinoma growth in vivo. Human MDA-MB-468 breast carcinoma cells were implanted subcutaneously on the flank of nude (nu/nu) mice and allowed to grow for 2 weeks to form palpable tumors (dotted blue line indicates size after 2 weeks). At that time, systemic delivery (0.25 μL/hr) of 400 μM recombinant GST-S4ED, GST alone or saline alone (no treatment) was initiated by surgical implantation of Alzet pumps on the behind the shoulder blades of the animals for 4 wks, followed by replacement with pumps containing fresh protein for an additional 4 wks. Tumor size was measured with calipers at 2 week intervals. Error bars denote S.D., 10 tumors/treatment group.

The inventor has tested the entire recombinant S4ED protein (as a GST-S4ED fusion protein) as an inhibitor against one of these carcinoma cells (the MDA-MB-468 cells) during tumor growth in immunocompromised nude (nu/nu) mice. Note that at 400 µM in the pump (estimated 2-3 µM in the blood), the GST-S4ED begins to disrupts the growth of MDA-MB-468 breast carcinoma after 2 weeks, with the tumor growth leveling off after that time, while the untreated tumors or tumors treated with GST alone continue to grow (FIG. 10).

Example 3

Discussion

Epithelial cells rely on the α6β4 integrin to form hemidesmosomes, anchoring the epithelial layer to the ECM and helping it to resist frictional forces. However, during wound healing or normal epithelia, or in transformed carcinomas overexpressing the EGFR, the hemidesmosomes break down in response to EGFR signaling and the free integrin associates with the EGFR. EGFR causes phosphorylation of the β4 subunit in its signaling domain, leading to cell proliferation, survival (if a carcinoma) and invasion. The current work shows that this mechanism relies on association of the integrin with EGFR and Sdc4. Sdc4 engages the cytoplasmic domain of the integrin, ostensibly bringing it to the membrane where it becomes phosphorylated. But a site in the extracellular domain of Sdc4 is also essential and appears responsible for capturing α6β4 integrin and EGFR as a signaling complex. Competition with either full-length Sdc4 ectodomain expressed as a recombinant protein, or competition with a peptide consisting of amino acids 87-131 in Sdc4 (human sequence) serves to block the EGF stimulated migration of epithelia, and disrupts the proliferation and survival of tumor cells that depend on this mechanism. The inventor proposes that this sequence, called synstatin-EGFR or $SSTN_{EGFR}$, is a new anti-cancer therapeutic. It acts on breast carcinoma cells, as well as on squamous cell carcinoma—two examples of carcinoma that rely on this signaling mechanism, apparently by competing for the assembly of α6β4 and EGFR with Sdc4. Blockade of this assembly, at a minimum, prevents activation of the α6β4 integrin and may have additional effects on activation of the EGFR as well. Importantly, although blockade of assembly disrupts the migration of normal cells, it does not lead to cell death as it does for tumor cells.

The region of Sdc4 that contains the active motif for $SSTN_{EGFR}$ has previously been recognized to bind cell surface receptors on other types of cells (McFall et al., 1997; 1998; Whiteford and Couchman, 2006). demonstrated that recombinant Sdc4 ectodomain used as an attachment substratum captured fibroblasts and endothelial cells, indicating that receptors on those cells interact with this protein. Expressing truncated versions of the protein, she identified the active region as amino acids 78-131 (actually referred to as 56-109 in her work (McFall et al., 1997; 1998) after subtraction of the signal peptide sequence), similar to the present work. However, there are several important differences between the reports of McFall et al. and the present work. First, McFall envisioned that shed Sdc4 might act as a matrix-bound ligand and thus provide a site for cell-matrix adhesion. The present work proposes that Sdc4 acts as an organizer to cause assembly of receptors into signaling complexes in cis (e.g., on the same cell). McFall's finding has been followed up by work from Whiteford et al. (2006), again describing the protein as an adhesion ligand.

Secondly, McFall described the activity on fibroblasts and endothelial cells; this is in contrast to the present work as the α6β4 integrin—the target of the present work—is not expressed on fibroblasts, nor is it expressed on endothelial cells when they are grown in culture (Homan et al. 1998). Whiteford et al. (2006) also described the protein as a ligand for fibroblastic, endothelial and lymphoblastic cells, but reported that it fails to act as an adhesion ligand for epithelial cells, which express the α6β4 integrin. Thus, it seems that the assay devised by McFall et al. and Whiteford et al. was reporting on adhesion via a different receptor—one found on fibroblastic and not epithelial cells, whereas this report is for receptor(s) found on epithelia.

Last, McFall also tested truncation mutants of the active sequence for their ability to mimic binding to the surface of fibroblasts, finding that S4ED78-118 was completely inactive as a competitor for cell adhesion to full-length S4ED. In contrast, S4ED 98-131 could compete, but was 100-fold less active that S4ED78-131. This contrasts with the present findings (FIGS. 8A-C) in which S4ED 78-118 and S4ED98-131 equally exhibit ca. 10% competitive activity, suggesting that they are targeting a different site or set of receptors than McFall et al.

The inventor's conclusions from these findings are that the S4ED87-131 motif may be a structural unit that presents different binding motifs for capture of different receptors. Thus, he proposes that a specific set of amino acids within this region binds to (and competes for) a set of receptors on carcinoma cells that is distinct from the receptor(s) studied by McFall et al. and Whiteford et al. He envisions that this specific inhibitor will be highly specific for the Sdc4/α6β4/EGFR receptor complex and its role in promoting epithelial cancers and angiogenesis.

The α6β4 integrin appears to be expressed with HER2 and EGFR in the vasculature and lymphatics of tumors (Nikolopoulos et al., 2004; Amin et al., 2006; Bohling et al., 1996; Bruns et al., 2000; Kedar et al., 2002; Huang et al., 2002), potentially implicating the Sdc4-coupled mechanisms in angiogenesis. The role of the α6β4 integrin in vascular endothelial cells is not well appreciated, as vascular endothelial cells rapidly lose expression of α6β4 integrin when placed into culture, making it difficult to study (Homan et al., 1998). When expressed artificially in such cells, it is found that they rely on α6β4 integrin to activate Erk and NFκB signaling pathways and migrate to close scratch wounds when plated on LN332 (Nikolopoulos et al., 2004), similar to its role in normal epithelial cells. Work from mouse models of tumorigenesis in vivo are more clear, demonstrating that not only is the integrin expressed in tumor vasculature, but HER2 and EGFR are also expressed, especially in endothelial cells lining blood vessels surrounding tumors (Amin et al., 2006; Bruns et al., 2000; Kedar et al., 2002), and that HER2 and EGFR couple with the α6β4 integrin during tumor-induced angiogenesis (Nikolopoulos et al., 2004). Both Sdc1 and Sdc4 are expressed in the vasculature as well, including tumor vasculature (Beauvais et al., 2009; Echtermeyer et al., 2001; Partovian et al., 2008; Tkachenko et al., 2004). Thus, although the inventor has not yet studied its effects on tumor-induced angiogenesis, it is highly plausible that $SSTN_{EGFR}$ targets tumor angiogenesis as well as the growth, survival and invasion of the tumor cells themselves.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VII. REFERENCES

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Pat. No. 7,183,059
U.S. Pat. No. 7,192,713
U.S. Patent Appln. 2005/0015232
Agazie and Hayman, Mol. Cell. Biol., 23(21):7875-7886, 2003.
Amano et al., J. Biol. Chem., 275(30):22728-22735, 2000.
Amin et al., Cancer Res., 66(4):2173-2180, 2006.
Baciu and Goetinck, Mol. Biol. Cell, 6:1503-1513, 1995.
Beauvais et al., J. Cell Biol., 167(1):171-181, 2004.
Beauvais et al., J. Exp. Med., 206(3):691-705, 2009.
Beauvais and Rapraeger, J Cell Sci, 123(21): p. 3796-807, 2010.
Bernfield et al., Annu. Rev. Biochem., 68:729-777, 1999.
Bernfield et al., Annu. Rev. Cell Biol., 8:365-393, 1992.
Bertotti et al., Cancer Res., 65(23):10674-10679, 2005.
Bertotti et al., J. Cell Biol., 175(6):993-1003, 2006.
Bodanszky et al., J. Antibiot., 29(5):549-53, 1976.
Bohling et al., J Neuropathol Exp Neurol, 1996. 55(5): p. 522-7, 1996.
Bon et al., Breast Cancer Res, 9(1):203, 2007.
Boudreau et al., J. Cell Biol., 139(1):257-264, 1997.
Brooks et al., Cell, 79:1157-1164, 1994.
Bruns et al., Cancer Res., 60(11):2926-2935, 2000.
Carey et al., Exp. Cell Res., 214:12-21, 1994a.
Carey et al., J. Cell Biol., 124:161-170, 1994b.
Carey et al., Otolaryngol. Head Neck Surg., 96(3):221-230, 1987.
Carulli et al., J. Biol. Chem., 287(15):12204-12216, 2012.
Carvalho et al., Clinics (Sao Paulo), 65(10):1033-1036, 2010.
Cassell and Grandis, Expert Opin. Investig. Drugs, 19(6): 709-722, 2010.
Chang and Califano, J. Surg. Oncol., 97(8):640-643, 2008.
Choi and Chen, Cancer, 104(6):1113-1128, 2005.
Chung et al., Cancer Cell, 5(5):489-500, 2004.
Cohen et al., J. Med. Chem., 33:883-894, 1990.
Colorado et al., Cancer Res., 60(9):2520-2526, 2000.
Couchman et al., Int. Rev. Cytol., 207:113-150, 2001.
Dajee et al., Nature, 421(6923):639-643, 2003.
Dans et al., J. Biol. Chem., 276(2):1494-1502, 2001.
Datta et al., Genes Dev., 13(22):2905-2927, 1999.
David et al., J. Cell Biol., 118(4):961-969, 1992.
Dent et al., Clin. Cancer Res., 13(15 Pt 1):4429-4434, 2007.
Dent et al., Mol. Biol. Cell, 10(8):2493-2506, 1999.
Diaz et al., Mod. Pathol., 18(9):1165-1175, 2005.
Dutta and Shaw, Cancer Res., 68(21):8779-8787, 2008.
Echtermeyer et al., J Clin Invest, 107(2): p. R9-R14, 2001.
Elenius et al., J. Cell Biol., 114(3):585-595, 1991.
Falcioni et al., Cancer Res., 46(11):5772-5778, 1986.
Falcioni et al., Exp. Cell Res., 236(1):76-85, 1997.
Folgiero et al., PLoS One, 3(2):e1592, 2008.

Friedlander et al., *Science*, 270:1500-1502, 1995.
Friedrichs et al., *Cancer Res.*, 55(4):901-906, 1995.
Gallo et al., *J. Invest. Dermatol.*, 107(5):676-683, 1996.
Gambaletta et al., *J. Biol. Chem.*, 275(14):10604-10610, 2000.
Giancotti, *Trends Pharmacol. Sci.*, 28(10):506-511, 2007.
Ginos et al., *Cancer Res.*, 64(1):55-63, 2004.
Goldfinger et al., *J. Cell Biol.*, 141(1):255-265, 1998.
Goldfinger et al., *J. Cell Sci.*, 112(Pt 16):2615-2629, 1999.
Gotte et al., *Invest. Ophthal. Visual Sci.*, 43(4):1135-1141, 2002.
Grandis et al., *Oncogene*, 15(4):409-416, 1997.
Granes et al., *Exp. Cell Res.*, 248:439-456, 1999.
Gronenborn et al., *Anal. Chem.*, 62(1):2-15, 1990.
Guo et al., *Cell*, 126(3):489-502, 2006.
Haffty et al., *J. Clin. Oncol.*, 24(36):5652-5657, 2006.
Hansen et al., *J. Cell Biol.*, 126:811-819, 1994.
Haupt et al., *Arch. Pathol. Lab. Med.*, 134(1):130-133, 2010.
Herschkowitz et al., *Genome Biol.*, 8(5):R76, 2007.
Homan et al., *J Cell Sci*, 111(18): p. 2717-28, 1998.
Hopkinson and Jones, *Mol. Biol. Cell*, 11(1):277-286, 2000.
Huang et al., *Mol. Cancer Ther.*, 1(7):507-514, 2002.
Hynes and Lane, *Nat. Rev. Cancer*, 5(5): 341-354, 2005.
Hynes and MacDonald, *Curr. Opin. Cell Biol.*, 21(2):177-184, 2009.
Iba et al., *J. Cell Biol.*, 149:1143-1156, 2000.
Izzard et al., *Exp. Cell Res.*, 165:320-336, 1986.
Jackson, *Seminars in Oncology*, 24:L164-172, 1997.
Johnson et al., In: *Biotechnology And Pharmacy*, Pezzuto et al. (Eds.), Chapman and Hall, NY, 1993.
Jones et al., *J. Med. Chem.*, 39:904-917, 1996.
Kamphaus et al., *J. Biol. Chem.*, 275(2):1209-1215, 2000.
Kedar et al., *Clin. Cancer Res.*, 8(11):3592-3600, 2002.
Khan et al., *J. Biol. Chem.*, 263:11314-113148, 1988.
Kimmel and Carey, *Cancer Res.*, 46(7):3614-3623, 1986.
Klass et al., *J. Cell Sci.*, 113:493-506, 2000.
Lebakken, and Rapraeger, *J. Cell Biol.*, 132:1209-1221, 1996.
Liu et al., *J. Biol. Chem.*, 273:22825-22832, 1998.
Livasy et al., *Mod. Pathol.*, 19(2):264-271, 2006.
Lu et al., *Clin. Cancer Res.*, 14(4):1050-1058, 2008.
Maeshima et al., *J. Biol. Chem.*, 275(28):21340-21348, 2000.
Mainiero et al., *EMBO J.*, 16(9): 2365-2375, 1997.
Mainiero et al., *J. Cell Biol.*, 134(1):241-253, 1996.
Marinkovich et al., *J. Biol. Chem.*, 267(25):17900-17906, 1992.
Mariotti et al., *J. Cell Biol.*, 155(3):447-458, 2001.
Matsui et al., *J. Biol. Chem.*, 270(40):23496-23503, 1995.
McFall and Rapraeger, *J. Biol. Chem.*, 272:12901-12904, 1997.
McFall and Rapraeger, *J. Biol. Chem.*, 273:28270-28276, 1998.
McPherson, *J. Biol. Chem.*, 251:6300-6306, 1976.
Merdek et al., *J. Biol. Chem.*, 282(41):30322-30330, 2007.
Merrifield, *J. Am. Chem. Soc.*, 85:2149-2154, 1963.
Mertens et al., *J. Biol. Chem.*, 267(28):20435-20443, 1992.
Miranti and Brugge, *Nat. Cell Biol.*, 4:E83-90, 2002.
Myers et al., *Am. J. Pathology*, 161(6): 2099-2109, 2002.
Myers et al., *J. Cell Biol.*, 148(2): 343-351, 2000.
Navia et al., *Curr. Opin. Struct. Biol.*, 2:202-210, 1992.
Nievers et al., *Matrix Biol.*, 18(1):5-17, 1999.
Nikolopoulos et al., *Cancer Cell*, 6(5):471-483, 2004.
Oh et al., *J. Biol. Chem.*, 272:8133-8136, 1997a.
Oh et al., *J. Biol. Chem.*, 272:11805-11811, 1997b.
Oh et al., *J. Biol. Chem.*, 273:10624-10629, 1998.
Ohtake et al., *Br. J. Cancer*, 81:393-403, 1999.
O'Reilly et al., *Cell*, 79(2):315-328, 1994.
O'Reilly et al., *Cell*, 88(2):277-285, 1997.
Partovian et al., *Mol Cell*, 32(1): p. 140-9, 2008.
Patarroyo et al., *Semin. Cancer Biol.*, 12(3):197-207, 2002.
PCT Appln. PCT/US00/03745
PCT Appln. PCT/US00/14667
PCT Appln. PCT/US99/11913
PCT Appln. PCT/US99/18441
Peptide Synthesis, 1985
Perez-Ordonez et al., *J. Clin. Pathol.*, 59(5):445-453, 2006.
Perou et al., *Nature*, 406(6797):747-752, 2000.
Protective Groups in Organic Chemistry, 1973
Protein NMR Spectroscopy, Principles and Practice, J. Cavanagh et al., Academic Press, San Diego, 1996.
Rabinovitz et al., *Mol. Cell Biol.*, 24(10):4351-4360, 2004.
Rapraeger and Ott, *Curr. Opin. Cell Biol.*, 10(5):620-628, 1998.
Rapraeger, *J. Cell Biol.*, 149:995-998, 2000.
Remington's Pharmaceutical Sciences, 15th Ed., 1035-1038 and 1570-1580, 1990.
Remington's Pharmaceutical Sciences, 15th Ed., 3:624-652, 1990.
Roskelley et al., *Curr. Opin. Cell Biol.*, 7:736-747, 1995.
Russell et al., *J. Cell Sci.*, 116(Pt 17):3543-3556, 2003.
Santoro et al., *Dev. Cell.*, 5(2):257-271, 2003.
Saoncella et al., *Proc. Natl. Acad. Sci. USA*, 96:2805-2810, 1999.
Scaltriti and Baselga, *Clin. Cancer Res.*, 12(18):5268-5272, 2006.
Schafmeister et al., *J. Amer. Chem. Soc.*, 122(24) 5891-5892, 2000.
Schmidt-Ullrich et al., *Int. J. Radiat. Oncol. Biol. Phys.*, 29(4):813-819, 1994
Sehgal et al., *J. Biol. Chem.*, 281(46):35487-35498, 2006.
Shaw et al., *Cell*, 91(7):949-960, 1997.
Shaw, *Mol. Cell Biol.*, 21(15):5082-5093, 2001.
Singer et al., *J. Cell Biol.*, 104:573-584, 1987.
Solid Phase Peptide Synthelia, 1984
Streeter and Rees, *J. Cell Biol.*, 105:507-515, 1987.
Teng et al., *Breast Cancer Res.*, 13(2):R35, 2011.
Tkachenko et al., *J Cell Sci*, 117(15): p. 3189-99, 2004.
Tran et al., *Cancer Res.*, 68(8):2885-2894, 2008.
Trusolino et al., *Cell*, 107(5):643-654, 2001.
Tsuruta et al., *Curr. Med. Chem.*, 15(20):1968-1975, 2008.
Van Waes et al., *Cancer Res.*, 51(9):2395-2402, 1991.
Wang et al., *J. Biol. Chem.*, 285:13569-13579, 2010.
Weber, *Advances Protein Chem.*, 41:1-36, 1991.
Whiteford and Couchman, *J Biol Chem*, 281(43): p. 32156-63, 2006.
Wider, *BioTechniques*, 29:1278-1294, 2000.
Wilhelmsen et al., *Mol. Biol. Cell*, 18(9):3512-3522, 2007.
Wilhelmsen et al., *Mol. Biol. Cell*, 26(8):2877-2886, 2006.
Wolf et al., *J. Natl. Cancer Inst.*, 82(19):1566-1572, 1990
Woods and Couchman, *Curr. Opin. Cell Biol.*, 13:578-583, 2001.
Woods and Couchman, *Mol. Biol. Cell*, 5:183-192, 1994.
Woods et al., *Embo J.*, 5:665-670, 1986.
Yamashita et al., *J. Immunol.*, 162:5940-5948, 1999.
Yang et al., *Mol. Cell Biol.*, 30(22):5306-5317, 2010.
Zimmermann et al., *Radiat. Oncol.*, 1:11, 2006.

What is claimed is:

1. A peptide consisting of:
   (a) a peptide segment consisting of between 25 and 100 amino acid residues and comprising about 45 residues of SEQ ID NO:1 including residues 87-131 (SEQ ID NO:4), wherein one or more of the between 25 and 100 amino acids are D-amino acids; or
   (b) a peptide segment consisting of between 25 and 100 amino acid residues and comprising about 45 residues of SEQ ID NO:1 including residues 87-131 (SEQ ID NO:4), and a blocking agent that is attached to the amino terminal and/or carboxyl terminal residues of the peptide segment.

2. The peptide of claim 1, wherein said peptide segment is 45, 46, 47, 48, 49, 50, 51, 52, 53, 54, 55, 60, 65, 70, 75, 80, 85, 90, 95 or 100 amino acid residues in length.

3. The peptide of claim 1, wherein said peptide segment is between 45 and 54 amino acid residues in length.

4. The peptide of claim 1, wherein said peptide segment is between 45 and 65 amino acid residues in length.

5. The peptide of claim 1, wherein said peptide segment is between 45 and 75 amino acid residues in length.

6. The peptide of claim 1, wherein said peptide segment consists essentially of residues 87-131 of SEQ ID NO:1 (SEQ ID NO:4).

7. The peptide of claim 1, wherein said peptide segment consists of residues 87-131 of SEQ ID NO:1 (SEQ ID NO:4).

8. The peptide of claim 1, wherein said peptide segment consists essentially of residues 78-131 of SEQ ID NO:1 (SEQ ID NO:5).

9. The peptide of claim 1, wherein said peptide segment consists of residues 78-131 of SEQ ID NO:1 (SEQ ID NO:5).

10. The peptide of claim 1, wherein said peptide segment comprises all D amino acids, or a mixture of D and L amino acids.

11. A method of inhibiting scarring in a subject comprising administering to said subject the peptide of claim 1, whereby scarring is inhibited in the subject.

12. A method of inhibiting pathologic neovascularization in a subject comprising administering to said subject the peptide of claim 1, whereby pathological neovascularization is inhibited in the subject.

13. The method of claim 12, wherein said peptide segment is 45, 46, 47, 48, 49, 50, 51, 52, 53, 54, 55, 60, 65, 70, 75, 80, 85, 90, 95 or 100 amino acid residues in length.

14. The method of claim 12, wherein said peptide segment is between 45 and 54 amino acid residues in length, between 45 and 65 amino acid residues in length, or between 45 and 75 amino acid residues in length.

15. The method of claim 12, wherein said peptide segment consists essentially of residues 87-131 of SEQ ID NO:1 (SEQ ID NO:4).

16. The method of claim 12, wherein said peptide segment consists of residues 87-131 of SEQ ID NO:1 (SEQ ID NO:4).

17. The method of claim 12, wherein said peptide segment consists essentially of residues 78-131 of SEQ ID NO:1 (SEQ ID NO: 5).

18. The method of claim 12, wherein said peptide segment consists of residues 78-131 of SEQ ID NO:1 (SEQ ID NO:5).

19. The method of claim 12, wherein said peptide segment comprises all D amino acids, or a mixture of D and L amino acids.

20. The method of claim 12, wherein said peptide segment is between 31 and 40 residues in length.

21. The method of claim 12, wherein said pathological neovascularization involves activated vascular endothelial cells.

* * * * *